(12) United States Patent
Li et al.

(10) Patent No.: US 12,390,376 B2
(45) Date of Patent: Aug. 19, 2025

(54) MULTI-LAYER ABSORBENT CORES AND METHODS OF MANUFACTURE

(71) Applicant: KIMBERLY-CLARK (CHINA) CO., LTD., Shanghai (CN)

(72) Inventors: Man Li, Beijing (CN); TongTong Zhang, Beijing (CN); Yan Wang, Beijing (CN); JinHee Lee, Shanghai (CN); Qingchun Lu, Beijing (CN)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1128 days.

(21) Appl. No.: 16/969,221

(22) PCT Filed: Feb. 28, 2018

(86) PCT No.: PCT/CN2018/077509
§ 371 (c)(1),
(2) Date: Aug. 12, 2020

(87) PCT Pub. No.: WO2019/165590
PCT Pub. Date: Sep. 6, 2019

(65) Prior Publication Data
US 2020/0405548 A1 Dec. 31, 2020

(51) Int. Cl.
*A61F 13/539* (2006.01)
*A61F 13/45* (2006.01)
(Continued)

(52) U.S. Cl.
CPC .... *A61F 13/539* (2013.01); *A61F 2013/4587* (2013.01); *A61F 13/4963* (2013.01);
(Continued)

(58) Field of Classification Search
CPC .................. A61F 13/15; A61F 13/539; A61F 2013/4587; A61F 2013/530182;
(Continued)

(56) References Cited

U.S. PATENT DOCUMENTS 5,019,069 A    5/1991   Klemp
5,211,641 A    5/1993   Roos et al.
(Continued)

FOREIGN PATENT DOCUMENTS

CA    2248633 A1    3/2000
CN    1158558 A     9/1997
(Continued)

OTHER PUBLICATIONS

CN_1163100_A translation (Year: 1997).*
(Continued)

*Primary Examiner* — Sarah Al Hashimi
*Assistant Examiner* — Hans Kaliher
(74) *Attorney, Agent, or Firm* — KIMBERLY-CLARK WORLDWIDE, INC.

(57) ABSTRACT

Absorbent cores comprising a layered structure and methods of manufacture are disclosed. In one embodiment, an absorbent body may comprise a top layer comprising a liquid permeable web material, a bottom layer comprising a web material, and a reinforcement layer disposed between the top layer and the bottom layer. The absorbent body may further comprise a first absorbent layer disposed between the reinforcement layer and the bottom layer, the first absorbent layer comprising absorbent material which comprises substantially only superabsorbent material and a second absorbent layer disposed between the top layer and the reinforcement layer, the second absorbent layer comprising absorbent material which comprises absorbent material. The body may also comprise adhesive disposed between the top layer and the second absorbent layer, between the second absorbent layer and the reinforcement layer, and between the first absorbent layer and the bottom layer.

14 Claims, 14 Drawing Sheets

(51) Int. Cl.
*A61F 13/496* (2006.01)
*A61F 13/53* (2006.01)

(52) U.S. Cl.
CPC .............. *A61F 2013/530182* (2013.01); *A61F 2013/530481* (2013.01); *A61F 2013/53908* (2013.01)

(58) Field of Classification Search
CPC .......... A61F 2013/530481; A61F 2013/53908; A61F 2013/53445
See application file for complete search history.

(56) References Cited

U.S. PATENT DOCUMENTS

| | | | |
|---|---|---|---|
| 5,248,309 | A | 9/1993 | Serbiak et al. |
| 5,248,524 | A | 9/1993 | Soderlund |
| 5,324,278 | A | 6/1994 | Visscher et al. |
| 5,380,310 | A | 1/1995 | Mitrani |
| 5,422,169 | A | 6/1995 | Roe |
| 5,423,786 | A | 6/1995 | Fung et al. |
| 5,423,787 | A | 6/1995 | Kjellberg |
| 5,429,627 | A | 7/1995 | Johnson et al. |
| 5,447,507 | A | 9/1995 | Yamamoto |
| 5,447,677 | A | 9/1995 | Griffoul et al. |
| 5,454,800 | A | 10/1995 | Hirt et al. |
| 5,460,623 | A | 10/1995 | Emenaker et al. |
| 5,556,392 | A | 9/1996 | Koczab |
| 5,562,646 | A * | 10/1996 | Goldman ................ A61L 15/42 428/339 |
| 5,611,879 | A | 3/1997 | Morman |
| 5,649,916 | A | 7/1997 | Dipalma et al. |
| 5,674,214 | A | 10/1997 | Visscher et al. |
| 5,722,967 | A * | 3/1998 | Coles .................... A61F 13/539 604/385.04 |
| 5,728,084 | A | 3/1998 | Palumbo et al. |
| 5,733,274 | A | 3/1998 | Osborn |
| 5,769,836 | A | 6/1998 | Klemp |
| 5,776,121 | A | 7/1998 | Roe et al. |
| 5,821,179 | A * | 10/1998 | Masaki ............... A61F 13/15203 442/381 |
| 5,897,544 | A | 4/1999 | Ronnberg |
| 5,900,109 | A | 5/1999 | Sanders et al. |
| 5,910,137 | A | 6/1999 | Clark et al. |
| 6,024,822 | A | 2/2000 | Alper et al. |
| 6,050,984 | A | 4/2000 | Fujioka et al. |
| 6,068,620 | A * | 5/2000 | Chmielewski .... A61F 13/53418 604/370 |
| 6,160,197 | A | 12/2000 | Lassen et al. |
| 6,162,959 | A | 12/2000 | O'Connor |
| 6,170,393 | B1 | 1/2001 | Hook et al. |
| 6,329,565 | B1 | 12/2001 | Dutkiewicz et al. |
| 6,372,952 | B1 | 4/2002 | Lash et al. |
| 6,417,120 | B1 | 7/2002 | Mitchler et al. |
| 6,475,199 | B1 | 11/2002 | Gann et al. |
| 6,506,959 | B2 | 1/2003 | Hamajima et al. |
| 6,566,578 | B1 | 5/2003 | Glaug et al. |
| 6,569,137 | B2 | 5/2003 | Suzuki et al. |
| 6,602,234 | B2 | 8/2003 | Klemp et al. |
| 6,613,955 | B1 | 9/2003 | Lindsay et al. |
| 6,632,209 | B1 | 10/2003 | Chmielewski |
| 6,638,260 | B2 | 10/2003 | Mishima |
| 6,645,186 | B2 | 11/2003 | Otsubo |
| 6,652,499 | B1 | 11/2003 | Edgren et al. |
| 6,666,851 | B2 | 12/2003 | Otsubo et al. |
| 6,673,985 | B2 | 1/2004 | Mizutani et al. |
| 6,677,498 | B2 * | 1/2004 | Chen ................ A61F 13/53743 604/385.01 |
| 6,689,416 | B2 | 2/2004 | Delzer et al. |
| 6,733,484 | B2 | 5/2004 | Van Gompel et al. |
| 6,790,798 | B1 | 9/2004 | Suzuki et al. |
| 6,794,557 | B1 | 9/2004 | Klemp et al. |
| 6,797,360 | B2 | 9/2004 | Varona |
| 6,822,135 | B2 | 11/2004 | Soerens et al. |
| 6,852,101 | B2 | 2/2005 | Damaghi et al. |
| 6,878,138 | B2 | 4/2005 | Tsuji et al. |
| 6,888,044 | B2 | 5/2005 | Fell et al. |
| 6,902,552 | B2 | 6/2005 | Vangompel et al. |
| 6,955,667 | B1 | 10/2005 | Tanaka et al. |
| 6,964,803 | B2 | 11/2005 | Krautkramer et al. |
| 7,008,408 | B2 | 3/2006 | Otsubo |
| 7,022,114 | B2 | 4/2006 | Fernfors et al. |
| 7,090,667 | B2 | 8/2006 | Fell et al. |
| 7,108,916 | B2 | 9/2006 | Ehrnsperger et al. |
| 7,121,818 | B2 | 10/2006 | Driskell |
| 7,169,136 | B2 | 1/2007 | Otsubo et al. |
| 7,172,583 | B2 | 2/2007 | Otsubo et al. |
| 7,226,437 | B2 | 6/2007 | Sasaki et al. |
| 7,232,300 | B2 | 6/2007 | Walter et al. |
| 7,247,215 | B2 | 7/2007 | Schewe et al. |
| 7,294,591 | B2 | 11/2007 | Soerens et al. |
| 7,326,193 | B2 | 2/2008 | Shimada et al. |
| 7,344,522 | B2 | 3/2008 | Suzuki et al. |
| 7,378,566 | B2 | 5/2008 | Soerens et al. |
| 7,458,960 | B2 | 12/2008 | Otsubo et al. |
| 7,520,874 | B2 | 4/2009 | Koyama et al. |
| 7,615,039 | B2 | 11/2009 | Rosenfeld et al. |
| 7,662,460 | B2 | 2/2010 | Herfert et al. |
| 7,695,461 | B2 | 4/2010 | Rosenfeld et al. |
| 7,708,727 | B2 | 5/2010 | Woltman et al. |
| 7,717,150 | B2 | 5/2010 | Manabe et al. |
| 7,722,590 | B2 | 5/2010 | Tsuji et al. |
| 7,727,212 | B2 | 6/2010 | Sakai et al. |
| 7,767,875 | B2 | 8/2010 | Olson et al. |
| 7,772,457 | B2 | 8/2010 | Ohtsuka et al. |
| 7,811,270 | B2 | 10/2010 | Rosenfeld et al. |
| 7,842,021 | B2 | 11/2010 | Wood et al. |
| 7,847,145 | B2 * | 12/2010 | Kurita ................. A61F 13/535 604/382 |
| 7,855,314 | B2 | 12/2010 | Hanao et al. |
| 7,884,259 | B2 | 2/2011 | Hanao et al. |
| 7,887,527 | B2 | 2/2011 | Hayashi et al. |
| 7,935,299 | B2 | 5/2011 | Walsh et al. |
| 7,955,536 | B2 | 6/2011 | Sawyer et al. |
| 7,959,622 | B2 | 6/2011 | Kudo et al. |
| 8,163,124 | B2 * | 4/2012 | Moriura ............. A61F 13/5323 156/276 |
| 8,173,858 | B2 | 5/2012 | Kuroda et al. |
| 8,178,035 | B2 | 5/2012 | Edvardsson et al. |
| 8,182,736 | B2 | 5/2012 | Edvardsson |
| 8,183,430 | B2 | 5/2012 | Hakansson et al. |
| 8,207,395 | B2 | 6/2012 | Soerens et al. |
| 8,251,966 | B2 | 8/2012 | Kudo et al. |
| 8,277,432 | B2 | 10/2012 | Bergstrom et al. |
| 8,361,047 | B2 | 1/2013 | Mukai et al. |
| 8,466,334 | B2 | 6/2013 | Takeuchi et al. |
| 8,480,387 | B2 | 7/2013 | Alkmin et al. |
| 8,556,875 | B2 | 10/2013 | Takahashi et al. |
| 8,591,490 | B2 | 11/2013 | Kudo et al. |
| 8,616,867 | B2 | 12/2013 | Brown et al. |
| 8,691,040 | B2 | 4/2014 | Yamamoto |
| 8,754,286 | B2 | 6/2014 | Bergstrom et al. |
| 8,852,381 | B2 | 10/2014 | Nhan et al. |
| 8,859,844 | B2 | 10/2014 | Takeuchi et al. |
| 8,871,123 | B2 | 10/2014 | de Carvalho et al. |
| 8,968,263 | B2 | 3/2015 | Watabe et al. |
| 8,998,871 | B2 | 4/2015 | Kuroda et al. |
| 9,056,034 | B2 * | 6/2015 | Akiyama .......... A61F 13/49473 |
| 9,066,838 | B2 * | 6/2015 | Hippe ................. A61F 13/514 |
| 9,072,634 | B2 | 7/2015 | Hundorf et al. |
| 9,216,116 | B2 | 12/2015 | Roe et al. |
| 9,238,089 | B2 | 1/2016 | Chmielewski et al. |
| 9,326,896 | B2 | 5/2016 | Schäfer et al. |
| 9,375,506 | B2 | 6/2016 | Konishi et al. |
| 9,468,566 | B2 | 10/2016 | Rosati et al. |
| 9,549,858 | B2 | 1/2017 | Yang |
| 9,730,843 | B2 | 8/2017 | Rosati et al. |
| 9,750,651 | B2 | 9/2017 | Bianchi et al. |
| 9,757,284 | B2 | 9/2017 | Tsang et al. |
| 9,782,305 | B2 | 10/2017 | Mukai et al. |
| 9,782,306 | B2 | 10/2017 | Tsang et al. |
| 9,782,307 | B2 | 10/2017 | Blessing et al. |
| 9,789,009 | B2 | 10/2017 | Joseph |
| 9,789,011 | B2 | 10/2017 | Roe et al. |

(56) References Cited

U.S. PATENT DOCUMENTS

| | | | |
|---|---|---|---|
| 9,789,012 B2 | 10/2017 | Chmielewski et al. |
| 9,789,014 B2 | 10/2017 | Wright et al. |
| 9,889,050 B2 | 2/2018 | Arayama et al. |
| 9,913,763 B2 | 3/2018 | Ryu et al. |
| 10,071,002 B2 | 9/2018 | Bianchi et al. |
| 10,098,795 B2 | 10/2018 | Mukai et al. |
| 10,137,039 B2 | 11/2018 | Stelzig et al. |
| 10,137,040 B2 | 11/2018 | Ehrnsperger et al. |
| 10,201,462 B2 | 2/2019 | Wright et al. |
| 10,441,481 B2 | 10/2019 | Bianchi et al. |
| 10,456,305 B2 | 10/2019 | Ehrnsperger et al. |
| 10,543,130 B2 | 1/2020 | Raycheck et al. |
| 10,675,191 B2 | 6/2020 | Suzuki et al. |
| 10,687,994 B2 | 6/2020 | Chmielewski et al. |
| 2001/0006089 A1 | 7/2001 | Ando et al. |
| 2001/0039405 A1 | 11/2001 | Keuhn et al. |
| 2002/0007165 A1 | 1/2002 | Proglhof et al. |
| 2002/0133131 A1 | 9/2002 | Rangachari et al. |
| 2003/0060792 A1 | 3/2003 | Harriz et al. |
| 2003/0084983 A1 | 5/2003 | Rangachari et al. |
| 2003/0098115 A1 | 5/2003 | Dodge et al. |
| 2003/0129915 A1 | 7/2003 | Harriz |
| 2003/0135176 A1 | 7/2003 | Delzer et al. |
| 2003/0143376 A1 | 7/2003 | Toyoshima et al. |
| 2003/0187413 A1 | 10/2003 | Fell |
| 2003/0236512 A1 | 12/2003 | Baker |
| 2004/0054342 A1 | 3/2004 | Newbill et al. |
| 2004/0253894 A1 | 12/2004 | Fell et al. |
| 2005/0124961 A1 | 6/2005 | Morman et al. |
| 2005/0186351 A1 | 8/2005 | Fung et al. |
| 2006/0004334 A1 | 1/2006 | Schlinz et al. |
| 2006/0020250 A1 | 1/2006 | Chester et al. |
| 2006/0040579 A1 | 2/2006 | Sheldon et al. |
| 2006/0058747 A1 | 3/2006 | Nguyen et al. |
| 2006/0184149 A1 | 8/2006 | Kasai et al. |
| 2006/0204723 A1 | 9/2006 | Bentley et al. |
| 2006/0206072 A1 | 9/2006 | Malakouti et al. |
| 2006/0206074 A1 | 9/2006 | Bernal et al. |
| 2006/0266467 A1 | 11/2006 | Mlinar |
| 2007/0142802 A1* | 6/2007 | Suzuki ............... A61F 13/5323 604/385.28 |
| 2007/0244455 A1 | 10/2007 | Hansson et al. |
| 2008/0082075 A1 | 4/2008 | Morrell-Schwartz |
| 2008/0167634 A1 | 7/2008 | Kouta et al. |
| 2009/0087636 A1 | 4/2009 | Yasuda et al. |
| 2010/0032860 A1 | 2/2010 | Hernandez et al. |
| 2011/0152809 A1 | 6/2011 | Carlucci et al. |
| 2011/0184365 A1 | 7/2011 | Röttger et al. |
| 2011/0313384 A1* | 12/2011 | Akiyama ............ A61F 13/5323 604/378 |
| 2012/0226253 A1* | 9/2012 | Urushihara ........... A61F 13/539 604/374 |
| 2012/0232508 A1 | 9/2012 | Urushihara |
| 2012/0316524 A1 | 12/2012 | Thomann et al. |
| 2013/0184666 A1 | 7/2013 | Sasayama et al. |
| 2014/0276510 A1* | 9/2014 | Ducker ................ A61L 15/58 604/365 |
| 2014/0308483 A1 | 10/2014 | Li |
| 2015/0045756 A1* | 2/2015 | Wright ............. A61F 13/53713 156/73.6 |
| 2015/0065974 A1 | 3/2015 | Michiels et al. |
| 2015/0174280 A1 | 6/2015 | Stelzig et al. |
| 2015/0209196 A1 | 7/2015 | Li |
| 2015/0282992 A1 | 10/2015 | Deng et al. |
| 2015/0313769 A1 | 11/2015 | Dahl et al. |
| 2015/0342796 A1 | 12/2015 | Bianchi et al. |
| 2015/0342797 A1 | 12/2015 | Jackels |
| 2015/0342798 A1 | 12/2015 | Jackels |
| 2015/0342799 A1 | 12/2015 | Michiels et al. |
| 2015/0342801 A1 | 12/2015 | Bianchi et al. |
| 2016/0040337 A1 | 2/2016 | Dutkiewicz et al. |
| 2016/0158401 A1 | 6/2016 | Tai et al. |
| 2016/0235594 A1 | 8/2016 | Ehrnsperger et al. |
| 2016/0235595 A1 | 8/2016 | Ehrnsperger et al. |
| 2016/0235596 A1 | 8/2016 | Ehrnsperger et al. |
| 2016/0235603 A1 | 8/2016 | Ehrnsperger et al. |
| 2016/0235604 A1 | 8/2016 | Ehrnsperger et al. |
| 2016/0235605 A1 | 8/2016 | Ehrnsperger et al. |
| 2016/0270987 A1 | 9/2016 | Stiehl et al. |
| 2017/0056255 A1 | 3/2017 | Fites et al. |
| 2017/0102306 A1 | 4/2017 | Dagher et al. |
| 2017/0128276 A1 | 5/2017 | Scaife |
| 2017/0135870 A1 | 5/2017 | Kamphus |
| 2017/0135871 A1 | 5/2017 | Kamphus |
| 2017/0281423 A1 | 10/2017 | Panayotova et al. |
| 2017/0312145 A1 | 11/2017 | Bianchi et al. |
| 2017/0312146 A1 | 11/2017 | Bianchi et al. |
| 2017/0312147 A1 | 11/2017 | Bianchi et al. |
| 2018/0064583 A1* | 3/2018 | Van De Maele ......... B32B 5/18 |
| 2018/0185203 A1 | 7/2018 | Mukai et al. |
| 2018/0207039 A1 | 7/2018 | Kreuzer et al. |
| 2018/0256415 A1 | 9/2018 | Miao et al. |
| 2018/0344541 A1 | 12/2018 | Ito et al. |
| 2019/0046368 A1 | 2/2019 | Peri et al. |
| 2019/0053956 A1 | 2/2019 | Nakamura et al. |
| 2019/0076307 A1 | 3/2019 | Takashima et al. |
| 2019/0358097 A1 | 11/2019 | Chmielewski et al. |
| 2020/0253796 A1 | 8/2020 | Chmielewski et al. |
| 2020/0337914 A1* | 10/2020 | Onishi ................. A61F 13/539 |

FOREIGN PATENT DOCUMENTS

| | | | |
|---|---|---|---|
| CN | 1163100 A * | 10/1997 | |
| CN | 1336868 A | 2/2002 | |
| CN | 1215825 C | 8/2005 | |
| CN | 200977230 Y | 11/2007 | |
| CN | 1676225 B | 11/2010 | |
| CN | 101061977 B | 6/2011 | |
| CN | 102438665 A | 5/2012 | |
| CN | 103007333 A | 4/2013 | |
| CN | 101641067 B | 5/2013 | |
| CN | 202984020 U | 6/2013 | |
| CN | 103300975 A | 9/2013 | |
| CN | 103491912 A | 1/2014 | |
| CN | 203417298 U | 2/2014 | |
| CN | 203436465 U | 2/2014 | |
| CN | 103637883 A | 3/2014 | |
| CN | 102361612 B | 6/2014 | |
| CN | 102573733 B | 7/2014 | |
| CN | 102573734 B | 7/2014 | |
| CN | 103892966 A | 7/2014 | |
| CN | 102083474 B | 8/2014 | |
| CN | 203790143 U | 8/2014 | |
| CN | 101849876 B | 9/2014 | |
| CN | 203815724 U | 9/2014 | |
| CN | 203885720 U | 10/2014 | |
| CN | 102781384 B | 11/2014 | |
| CN | 104161623 A | 11/2014 | |
| CN | 103282001 B | 12/2014 | |
| CN | 204016630 U | 12/2014 | |
| CN | 104394823 A | 3/2015 | |
| CN | 102700179 B | 4/2015 | |
| CN | 103327942 B | 4/2015 | |
| CN | 104540488 A | 4/2015 | |
| CN | 204260925 U | 4/2015 | |
| CN | 104605995 A | 5/2015 | |
| CN | 104723618 A | 6/2015 | |
| CN | 204501258 U | 7/2015 | |
| CN | 103006385 B | 10/2015 | |
| CN | 102378615 B | 1/2016 | |
| CN | 105530900 A | 4/2016 | |
| CN | 205163419 U | 4/2016 | |
| CN | 103249385 B | 5/2016 | |
| CN | 105722485 A | 6/2016 | |
| CN | 205286723 U | 6/2016 | |
| CN | 205359815 U | 7/2016 | |
| CN | 105853068 A | 8/2016 | |
| CN | 103269664 B | 9/2016 | |
| CN | 103402470 B | 10/2016 | |
| CN | 106038084 A | 10/2016 | |
| CN | 103313683 B | 2/2017 | |
| CN | 106361506 A | 2/2017 | |
| CN | 205947928 U | 2/2017 | |

(56) References Cited

FOREIGN PATENT DOCUMENTS

| | | | |
|---|---|---|---|
| CN | 205947929 U | 2/2017 | |
| CN | 104470477 B | 4/2017 | |
| CN | 106821603 A | 6/2017 | |
| CN | 106880445 A | 6/2017 | |
| CN | 206214292 U | 6/2017 | |
| CN | 106937903 A | 7/2017 | |
| CN | 106974774 A | 7/2017 | |
| CN | 107625583 A | 1/2018 | |
| CN | 107802410 A | 3/2018 | |
| CN | 207745262 U | 8/2018 | |
| CN | 109568012 A | 4/2019 | |
| CN | 109620550 A | 4/2019 | |
| CN | 109758305 A | 5/2019 | |
| CN | 209032878 U | 6/2019 | |
| CN | 209075162 U | 7/2019 | |
| CN | 110547917 A | 12/2019 | |
| CN | 212439076 U | 2/2021 | |
| DE | 3620077 C2 | 2/1991 | |
| DE | 202012013572 U1 | 1/2018 | |
| EP | 0348978 A2 | 1/1990 | |
| EP | 0442223 B1 | 2/1995 | |
| EP | 0606208 B1 | 5/1996 | |
| EP | 0549781 B1 | 9/1996 | |
| EP | 0768070 A1 | 4/1997 | |
| EP | 0746296 B1 | 6/2001 | |
| EP | 1032337 B1 | 10/2004 | |
| EP | 2591758 A1 | 5/2013 | |
| EP | 2679210 A1 | 1/2014 | |
| EP | 3047827 B1 | 3/2018 | |
| EP | 3042639 B1 | 9/2018 | |
| EP | 2656826 B1 | 10/2018 | |
| FR | 2604064 B1 | 2/1991 | |
| GB | 2246373 A | 1/1992 | |
| GB | 2272916 A * | 6/1994 | ......... A61F 13/2051 |
| GB | 2306331 A | 5/1997 | |
| GB | 2366518 A | 3/2002 | |
| JP | 1993049658 A | 3/1993 | |
| JP | 1997313530 A | 12/1997 | |
| JP | 3145105 B2 | 3/2001 | |
| JP | 2004016373 A | 1/2004 | |
| JP | 2004329511 A | 11/2004 | |
| JP | 3607038 B2 | 1/2005 | |
| JP | 3705943 B2 | 10/2005 | |
| JP | 2006230714 A | 9/2006 | |
| JP | 3847680 B2 | 11/2006 | |
| JP | 3883915 B2 | 2/2007 | |
| JP | 4128029 B2 | 7/2008 | |
| JP | 4156171 B2 | 9/2008 | |
| JP | 4163133 B2 | 10/2008 | |
| JP | 4280187 B2 | 6/2009 | |
| JP | 4678632 B2 | 4/2011 | |
| JP | 4695332 B2 | 6/2011 | |
| JP | 4883924 B2 | 2/2012 | |
| JP | 4919734 B2 | 4/2012 | |
| JP | 5001099 B2 | 8/2012 | |
| JP | 2013042881 A | 3/2013 | |
| JP | 5175147 B2 | 4/2013 | |
| JP | 5329274 B2 | 10/2013 | |
| JP | 5372484 B2 | 12/2013 | |
| JP | 5374298 B2 | 12/2013 | |
| JP | 5789423 B2 | 10/2015 | |
| JP | 5926904 B2 | 5/2016 | |
| JP | 6062707 B2 | 1/2017 | |
| JP | 6073619 B2 | 2/2017 | |
| JP | 6074184 B2 | 2/2017 | |
| JP | 6148419 B2 | 6/2017 | |
| JP | 2017217468 A | 12/2017 | |
| JP | 6306450 B2 | 4/2018 | |
| JP | 2018050669 A | 4/2018 | |
| JP | 6382253 B2 | 8/2018 | |
| JP | 2018166941 A | 11/2018 | |
| JP | 6460828 B2 | 1/2019 | |
| JP | 6496567 B2 | 4/2019 | |
| JP | 2019141308 A | 8/2019 | |
| JP | 2019162300 A | 9/2019 | |
| JP | 2019187740 A | 10/2019 | |
| JP | 2019208849 A | 12/2019 | |
| JP | 2020000273 A | 1/2020 | |
| JP | 2020010851 A | 1/2020 | |
| WO | 2009150984 A1 | 12/2009 | |
| WO | 2012002557 A1 | 1/2012 | |
| WO | 2012105283 A1 | 8/2012 | |
| WO | 2012105284 A1 | 8/2012 | |
| WO | 2014084087 A1 | 6/2014 | |
| WO | 2015012155 A1 | 1/2015 | |
| WO | 2015129367 A1 | 9/2015 | |
| WO | 2015198662 A1 | 12/2015 | |
| WO | 2015198665 A1 | 12/2015 | |
| WO | 2016063638 A1 | 4/2016 | |
| WO | 2016104184 A1 | 6/2016 | |
| WO | 16115181 A1 | 7/2016 | |
| WO | 2017077750 A1 | 5/2017 | |
| WO | 2017110747 A1 | 6/2017 | |
| WO | 17171782 A1 | 10/2017 | |
| WO | 2018100650 A1 | 6/2018 | |
| WO | 2018112229 A1 | 6/2018 | |
| WO | 2018123684 A1 | 7/2018 | |
| WO | 2018173737 A1 | 9/2018 | |
| WO | 2019070009 A1 | 4/2019 | |
| WO | 2019092807 A1 | 5/2019 | |
| WO | 2019092810 A1 | 5/2019 | |
| WO | 2020117731 A1 | 6/2020 | |

OTHER PUBLICATIONS

Mölnlycke, "Molnlycke Health Care", http://www.molnlycke.us/see-the-proof/patented-design/5-unique-layers/.
Google, "Core Issues for Diapers: Thin is in", Sep. 28, 2015, https://index17.ch/en/news/core-issues-for-diapers-thin-is-in-195.
Edana, "Superabsorbent", https://www.edana.org/discover-nonwovens/how-they're-made/superabsorbents.

* cited by examiner

MULTI-LAYER ABSORBENT CORES AND METHODS OF MANUFACTURE

TECHNICAL FIELD

The present disclosure is directed to absorbent bodies, and more particularly to layered absorbent cores for use in absorbent articles.

BACKGROUND OF THE DISCLOSURE

People rely on disposable absorbent products in their everyday lives, including such articles as adult incontinence products, enuresis pants, training pants, and diapers. Many manufacturers seek to better meet the needs of users of such products. For example, there is a need to further improve fit, discretion, and leakage protection for many products.

One important component of many absorbent articles are the absorbent cores contained in such articles. These absorbent cores are generally responsible for capturing and retaining liquid bodily exudates, thereby preventing the exudates from leaking out of the absorbent article and further retaining the liquid away from a wearer's skin, which helps to promote the health of the skin. Advances in the structure and performance of absorbent cores to produce thinner products which uptake liquid more quickly and leak less are a continued important area of market desire.

SUMMARY OF THE DISCLOSURE

The present disclosure is directed to absorbent bodies, and more particularly to layered absorbent cores for use in absorbent articles.

In a first embodiment, an absorbent body may comprise a top layer comprising a liquid permeable web material, a bottom layer comprising a web material, a reinforcement layer disposed between the top layer and the bottom layer, a first absorbent layer disposed between the reinforcement layer and the bottom layer, the first absorbent layer comprising absorbent material which comprises substantially only superabsorbent material, and a second absorbent layer disposed between the top layer and the reinforcement layer, the second absorbent layer comprising absorbent material which comprises absorbent material. The body may further comprise adhesive disposed between the top layer and the second absorbent layer, between the second absorbent layer and the reinforcement layer, and between the first absorbent layer and the bottom layer.

In a second embodiment, the absorbent material of the second absorbent layer of the first embodiment may comprise substantially only fibrous absorbent material.

In a third embodiment, the absorbent material of the second absorbent layer of the first embodiment may comprise substantially only superabsorbent material.

In a fourth embodiment, the absorbent material disposed within the second absorbent layer of the first embodiment may comprise between about 50% and about 80%, by weight, of superabsorbent material.

In a fifth embodiment, the absorbent material disposed within the second absorbent layer of the first embodiment may comprise a mixture of superabsorbent material and fibrous absorbent material, and the mixture may comprise a substantially uniform distribution of the superabsorbent material and the fibrous absorbent material.

In a sixth embodiment, the absorbent body of any of the first through fifth embodiments may further comprise superabsorbent material embedded within the reinforcement layer.

In a seventh embodiment, the superabsorbent material embedded within the reinforcement layer of the sixth embodiment may comprise between about 50% and about 80%, by weight, of the superabsorbent material embedded within the reinforcement layer and the superabsorbent material disposed within the first absorbent layer.

In an eighth embodiment, the superabsorbent material embedded within the reinforcement layer of any of the sixth and seventh embodiments may comprise between about 50% and about 65%, by weight, of the superabsorbent material embedded within the reinforcement layer and the superabsorbent material disposed within the first absorbent layer.

In a ninth embodiment, a total weight of absorbent material disposed within the second absorbent layer of any of the first through eighth embodiments may be between about 5.5 g and about 8.5 g.

In a tenth embodiment, a total weight of absorbent material embedded within the reinforcement layer and disposed within the first absorbent layer of any of the first through ninth embodiments may be between about 5.5 g and about 10.5 g.

In an eleventh embodiment, the total amount of absorbent material embedded within the reinforcement layer and disposed within the first absorbent layer of any of the sixth through tenth embodiments may be between about 50% and about 60%, by weight, of the total amount of absorbent material disposed within the first absorbent layer, the second absorbent layer, and embedded within the reinforcement layer.

In a twelfth embodiment, the absorbent body of any of the first through eleventh embodiments may further comprise an airlaid paper layer disposed between the second absorbent layer and the liquid permeable top-layer.

In a thirteenth embodiment, the absorbent body of any of the first through twelfth embodiments may further comprise an airlaid paper layer disposed between the first absorbent layer and the bottom layer.

In a fourteenth embodiment, the absorbent body of any of the first through thirteenth embodiments may further comprise a third absorbent layer, wherein the third absorbent layer may be disposed between the second absorbent layer and the top layer and wherein the third absorbent layer may comprise absorbent material comprising substantially only superabsorbent material.

In a fifteenth embodiment, the first absorbent layer of any of the first through fourteenth embodiments may comprise at least one channel region and a plurality of non-channel regions, and wherein an absorbent material content of the non-channel regions may be greater than an absorbent material content of the at least one channel region.

In a sixteenth embodiment, an absorbent body may comprise a top layer comprising a liquid permeable web material, a bottom layer comprising a web material, and a reinforcement layer comprising a nonwoven web material disposed between the top layer and the bottom layer, the reinforcement layer further comprising superabsorbent material embedded within the nonwoven web material. The body may further comprise a first absorbent layer disposed between the reinforcement layer and the bottom layer, the first absorbent layer comprising absorbent material which comprises substantially only superabsorbent material, a second absorbent layer disposed between the top layer and the reinforcement layer, the second absorbent layer comprising absorbent material which comprises a substantially uniform mixture of superabsorbent material and fibrous absorbent material, and adhesive disposed between the first airlaid paper layer and the second absorbent layer, between the second absorbent layer and the reinforcement layer, and between the first absorbent layer and the second airlaid paper layer. In some further embodiments, the first absorbent layer may comprise at least one channel region and a plurality of non-channel regions, and wherein an absorbent material content of the non-channel regions may be greater than an absorbent material content of the at least one channel region In a seventeenth embodiment, the absorbent body of the sixteenth embodiment may further comprise an airlaid paper layer disposed between the second absorbent layer and the liquid permeable top-layer.

In an eighteenth embodiment, the absorbent body of any of the sixteenth and seventeenth embodiments may further comprise an airlaid paper layer disposed between the first absorbent layer and the bottom layer.

In a nineteenth embodiment, the absorbent body of any of the sixteenth through eighteenth embodiments may further comprise a third absorbent layer, wherein the third absorbent layer may be disposed between the second absorbent layer and the top layer, and wherein the third absorbent layer may comprise absorbent material comprising substantially only superabsorbent material.

In a twentieth embodiment, the amount of superabsorbent material, by weight, embedded within the reinforcement layer and disposed within the first absorbent layer of any of the sixteenth through nineteenth embodiments may be between about two times and about three times the amount of superabsorbent material disposed within the second absorbent layer.

The above summary is not intended to describe each embodiment or every implementation of the present invention. Advantages and attainments, together with a more complete understanding of the disclosure, will become apparent and appreciated by referring to the following description and claims taken in conjunction with the accompanying drawings.

Figure 1:
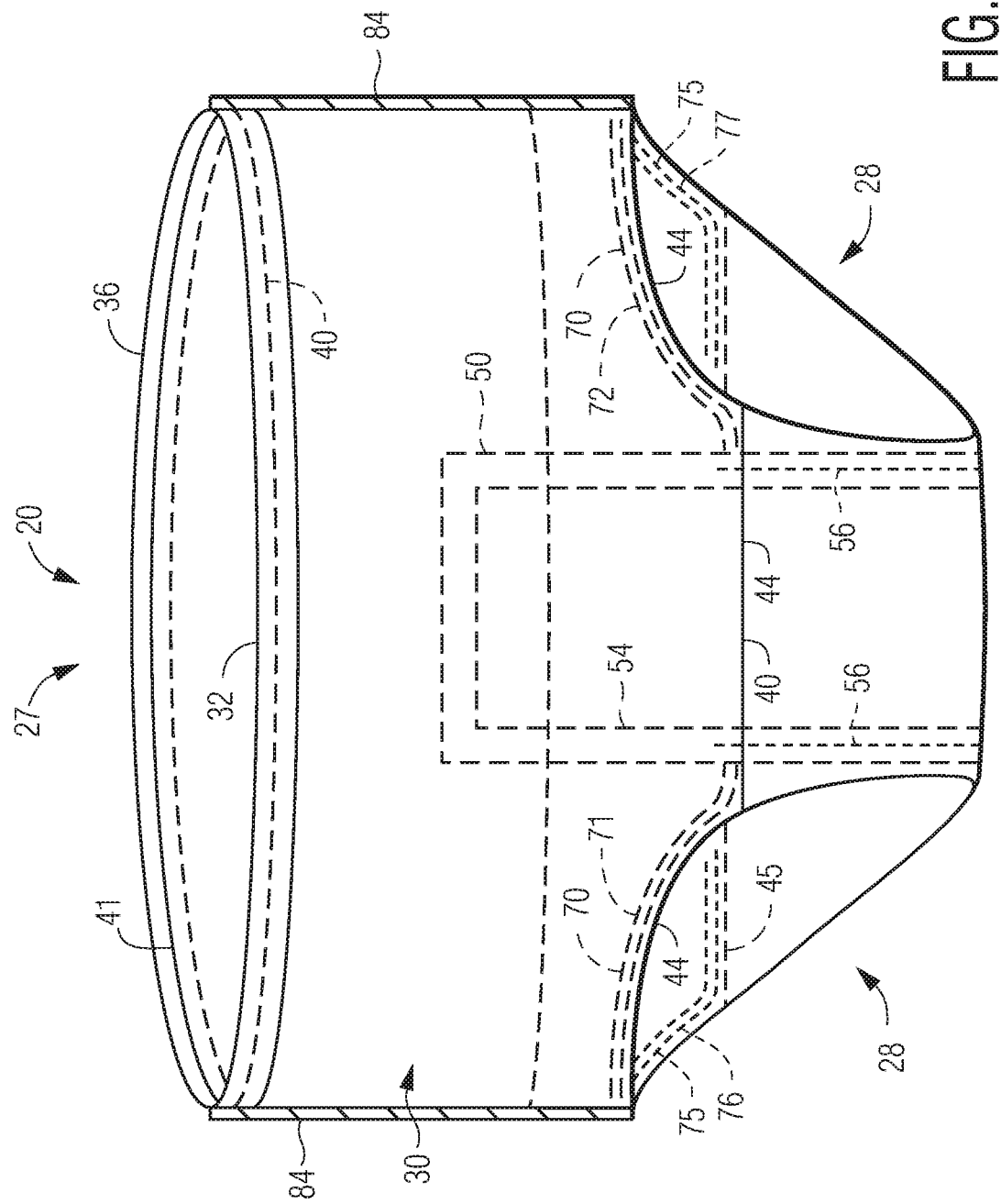
FIG. 1 is a perspective view of an exemplary absorbent article in a closed configuration, according to aspects of the present disclosure.

While the disclosure is amenable to various modifications and alternative forms, specifics thereof have been shown by way of example in the drawings and will be described in detail. It should is be understood, however, that the intention is not to limit aspects of the disclosure to the particular illustrative embodiments described. On the contrary, the intention is to cover all modifications, equivalents, and alternatives falling within the spirit and scope of the disclosure.

DETAILED DESCRIPTION OF THE DISCLOSURE

The following description should be read with reference to the drawings in which similar elements in different drawings are numbered the same. The description and the drawings, which are not necessarily to scale, depict illustrative embodiments and are not intended to limit the scope of the disclosure.

Within the context of this specification, each term or phrase below will include the following meaning or meanings. Additional terms are defined elsewhere in the specification.

"Absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, and incontinence products, and the like without departing from the scope of the present disclosure.

"Airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

"Bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

"Bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

"Coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 50 percent, more preferably by at least 100 percent, and still more preferably by at least 300 percent of its relaxed length and recover, upon release of an applied force, at least 50 percent of its elongation.

"Fibrous absorbent material" or "absorbent fibers" refers herein to natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber.

"Integral" is used to refer to various portions of a single unitary element rather than separate structures bonded to or placed with or placed near one another.

"Layer" when used in the singular can have the dual meaning of a single element or a plurality of elements.

"Machine direction" (MD) refers to the length of a fabric in the direction in which it is produced, as opposed to a "cross-machine direction" (CD) which refers to the width of a fabric in a direction generally perpendicular to the machine direction.

"Member" when used in the singular can have the dual meaning of a single element or a plurality of elements.

"Nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc.

"Spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

"Superabsorbent polymer," "superabsorbent material" "SAP", or "SAM" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

"Particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod like polyhedral, spherical or semi-spherical, rounded or semi-rounded, angular, irregular, et cetera.

"Particulate superabsorbent polymer" and "particulate superabsorbent polymer composition" refer to the form of superabsorbent polymer and superabsorbent polymer compositions in discrete form, wherein the "particulate superabsorbent polymer" and "particulate superabsorbent polymer compositions" may have a particle size of less than 1000 μm, or from about 150 μm to about 850 μm.

"Centrifuge Retention Capacity (CRC)" as used herein refers to the ability of the particulate superabsorbent polymer to retain liquid therein after being saturated and subjected to centrifugation under controlled conditions and is stated as grams of liquid retained per gram weight of the sample (g/g) as measured by the Centrifuge Retention Capacity Test set forth herein.

"Gel permeability" is a property of the mass of particles as a whole and is related to particle size distribution, particle shape, and the connectedness of the open pores between the particles, shear modulus, and surface modification of the swollen gel. In practical terms, the gel permeability of the superabsorbent polymer composition is a measure of how rapidly liquid flows through the mass of swollen particles. Low gel permeability indicates that liquid cannot flow readily through the superabsorbent polymer composition, which is generally referred to as gel blocking, and that any is forced flow of liquid (such as a second application of urine during use of the diaper) must take an alternate path (e.g., diaper leakage).

"Polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

"Vortex time" measures the amount of time in seconds required for 2 grams of a SAP to close a vortex created by stirring 50 milliliters of saline solution at 600 revolutions per minute on a magnetic stir plate. The time it takes for the vortex to close is an indication of the free swell absorbing rate of the SAP.

"Percent (%) by weight" or "% wt" as used herein and referring to components of the dry particulate superabsorbent polymer composition, is to be interpreted as based on the weight of the dry superabsorbent polymer composition, unless otherwise specified herein.

These terms may be defined with additional language in the remaining portions of the specification.

Figure 2:
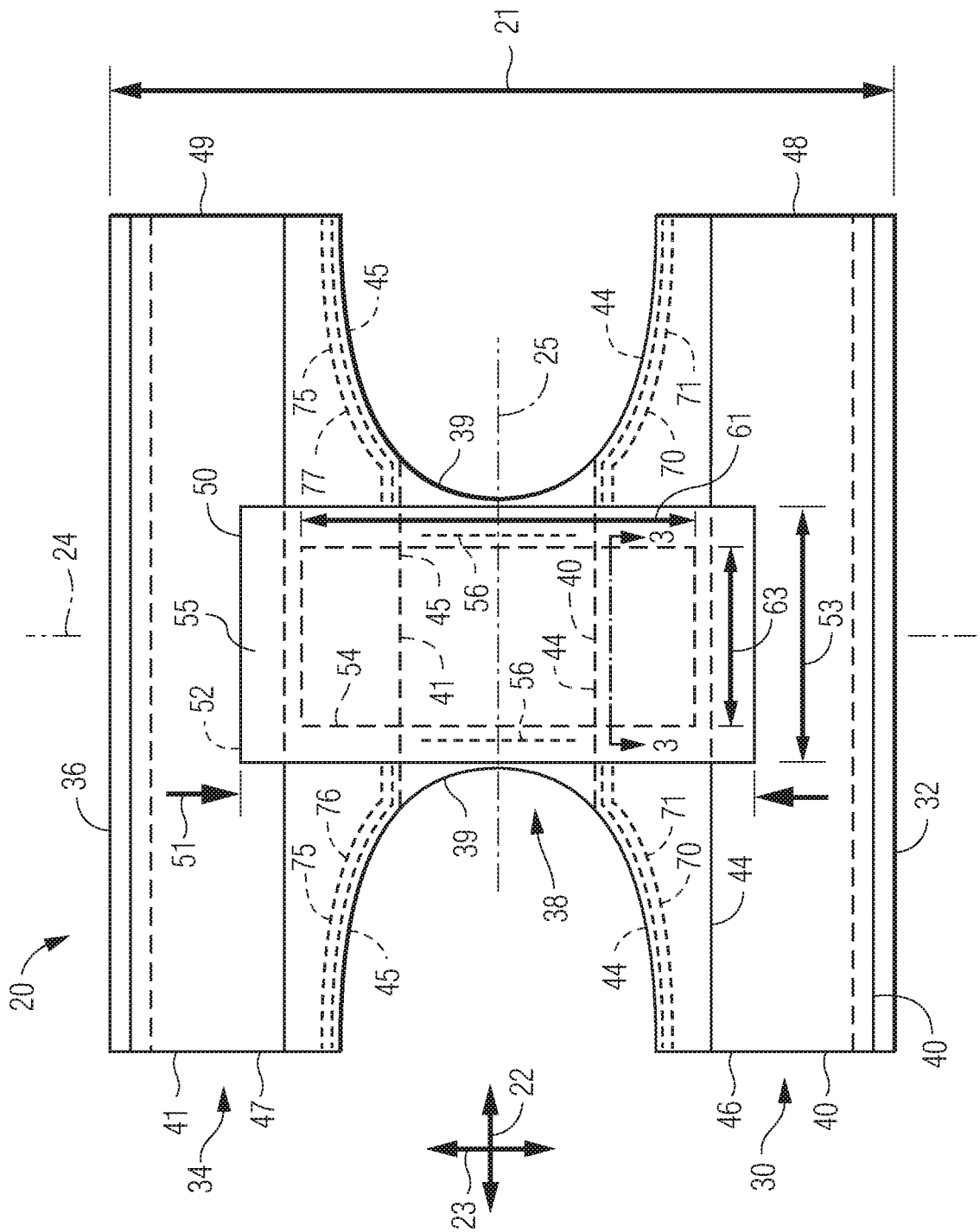
FIG. 2 is a plan view of the absorbent article of FIG. 1 in an open and laid flat configuration.

Referring to FIGS. 1-2, a garment 20 extends along a longitudinal direction 23 and a lateral direction 22 perpendicular to the longitudinal direction 23. As used in describing the various embodiments of the garment 20, according to aspects of the present disclosure, the terms "longitudinal" and "lateral" have their customary meaning, as indicated by the central longitudinal axis 24 and the central lateral axis 25. The central longitudinal axis 24 lies in the plane of the article when the article is in a fully stretched and laid-flat condition, while the front and rear panels are separated, and is generally parallel to a vertical plane that bisects a standing wearer into left and right body halves when the article is worn. The central lateral axis 25 lies in the plane of the article and is generally perpendicular to the central longitudinal axis 24. The garment 20 has a front region 30 defining a front waist end edge 32, a rear region 34 defining a rear waist end edge 36, and a crotch region 38 positioned longitudinally between the front region 30 and the rear region 34. The crotch region 38 defines two laterally opposed crotch side edges 39. The garment 20 defines a garment length 21 that extends from the front waist end edge 32 to the rear waist end edge 36.

The garment 20 includes a front panel 40 which defines a front panel leg edge 44 spaced longitudinally inward from the front waist end edge 32, and first and second laterally opposed front panel side edges 46, 48. The garment 20 also includes a rear panel 41 which defines a rear panel leg edge 45 spaced longitudinally inward from the rear waist end edge 36, and first and second is laterally opposed rear panel side edges 47, 49. "Longitudinally inward (or inboard)" as used to describe garment embodiments herein means in a direction longitudinally toward the central lateral axis 25. Likewise, "laterally inward (or inboard)" as used to describe garment embodiments herein means in a direction laterally toward the central longitudinal axis 24. The front panel 40 is longitudinally spaced apart from the rear panel 41. The specific structures of the front and rear panels 40, 41 are described below with respect to FIGS. 3A-11B.

A pair of side seams 84, 84 connects the front region 30 to the rear region 34, such that the garment 20 defines a waist opening 27 and a pair of leg openings 28. The side seams can be permanent but tearable, such as by way of adhesive, thermal, pressure, or ultrasonic bonding, or can be more readily releasable as well as refastenable, such as via the use of mechanical fastening elements.

The garment 20 may further include at least one front leg elastic member 70 disposed adjacent the front panel leg edge 44, and/or at least one rear leg elastic member 75 disposed adjacent the rear panel leg edge 45. Such leg elastic members 70 and/or 75 help to provide additional elastic support around the leg openings 28 to enhance the fit and leakage protection of the garment 20. Each leg elastic member 70, 75 can comprise a single ribbon, strand, or thread (or the like) of elastic material, or each can comprise two, three, or more ribbons, strands, or threads (or the like) of elastic material. Elastic ribbons, strands, threads, and the like suitable for use in disposable absorbent garments are known in the art, one example being LYCRA brand elastic filaments, available from the Dupont Corporation. In particular embodiments, the rear leg elastic member 75 and/or the front leg elastic member 70 extends laterally across the entire garment width. In other embodiments, such as that representatively illustrated in FIGS. 1 and 2, the rear leg elastic member 75 can comprise a pair of rear leg elastic members, such as first and second rear leg elastic members 76, 77 positioned on opposite sides of the absorbent composite 50. Similarly, the front leg elastic member 70 can comprise a pair of front leg elastic members, such as first and second front leg elastic members 71, 72 positioned on opposite sides of the absorbent composite 50. In preferred embodiments, such as that representatively illustrated in FIGS. 1 and 2, each rear leg elastic member 75 can comprise a plurality of elastomeric strands, and/or each front leg elastic member 70 can comprise a plurality of elastomeric strands.

In particular embodiments, an absorbent composite 50 is connected to and between the front panel 40 and the rear panel 41. The absorbent composite 50 may comprise a composite structure formed of a liquid impermeable barrier layer 52 defining a width 53 and a length 51, an absorbent body 54 comprising absorbent material, a liquid permeable liner 55, and/or crotch elastic members 56. As used herein, the term "absorbent material" may mean fibrous absorbent material, superabsorbent material (SAM), or a combination of both fibrous absorbent material and SAM. The absorbent body 54, in some embodiments, may comprise a layered structure that includes multiple regions of liquid-absorbing materials such as fibrous absorbent material and/or SAM. The absorbent body 54 defines a length 61 and a width 63. Further description of exemplary absorbent bodies 54 of the present disclosure is presented below with respect to FIGS. 3-12.

It should be understood that the exemplary pant-like garment 20 is only one possible example of an absorbent article which may be used with the described absorbent bodies 54 of the present disclosure. Such garments 20 as those shown in FIGS. 1 and 2 may be generally described as garments formed using a cross-machine direction (CD) manufacturing process. Alternative exemplary garments which may be used with the described absorbent bodies 54 may include those garments formed by a machine-direction (MD) manufacturing process. In general, the present disclosure is not meant to be limited to the specifically disclosed absorbent garments. Rather, the described absorbent bodies 54 may be used within any suitable chassis structure for retaining the described absorbent bodies 54 on a wearer. In even further contemplated embodiments, the described absorbent bodies 54 may not be used with any chassis structure at all. Rather, the absorbent bodies 54 may be constructed so as to be able to be placed directly in contact with a wearer's body—for example using body-adhesive disposed on a body-side surface of the absorbent bodies 54.

FIGS. 3-12 depict exemplary cross-sections of absorbent body 54 as viewed along line 3-3 of FIG. 2, according to aspects of the present disclosure. In general, the absorbent bodies 54 of the present disclosure may comprise multiple layers, including multiple, separate layers of absorbent material.

Figure 3:
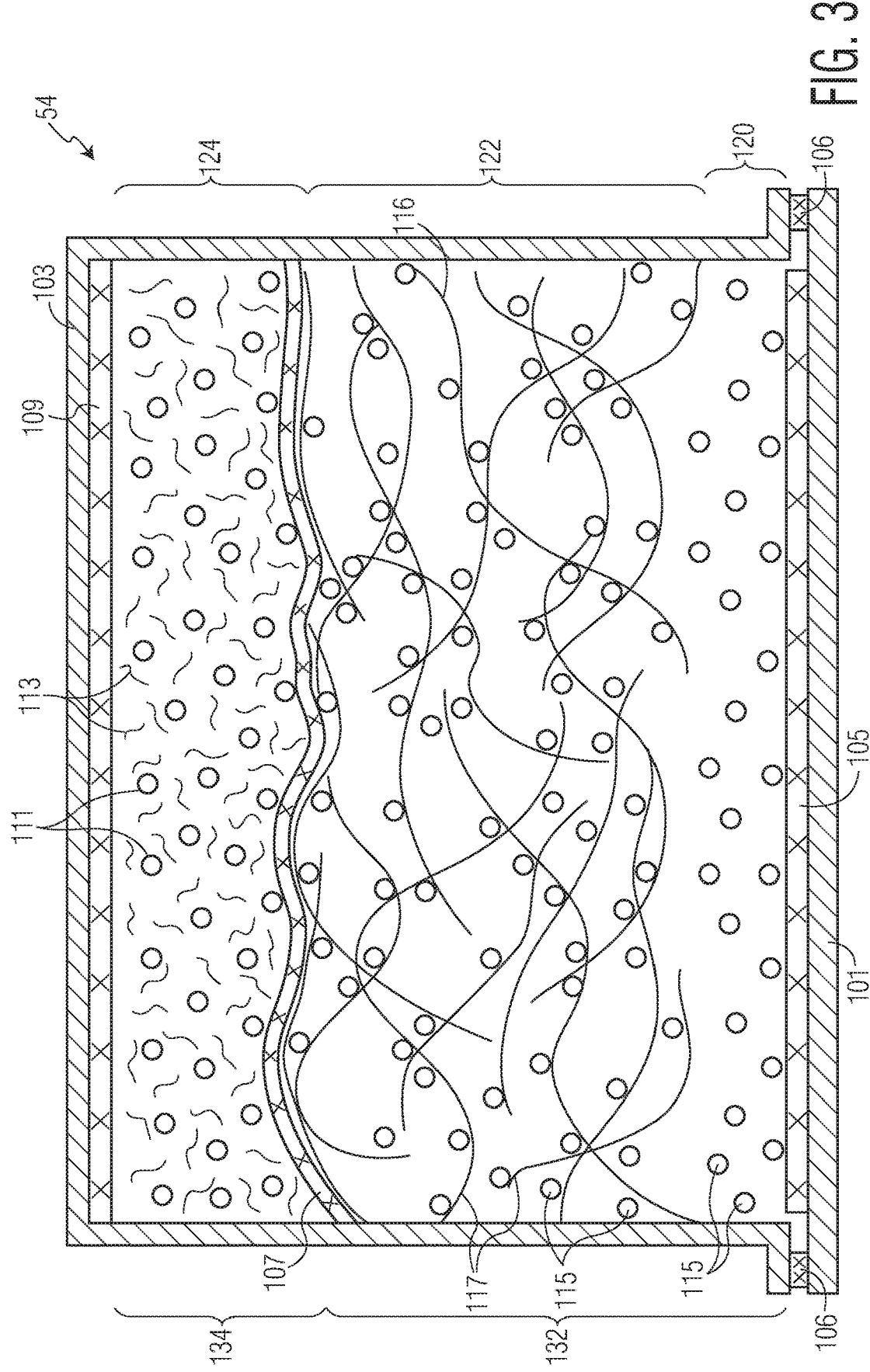
FIG. 3 is a cross-section of an exemplary absorbent body for use in an absorbent article, according to aspects of the present disclosure.

In the embodiment of FIG. 3, the exemplary absorbent body comprises both a bottom corewrap sheet 101 and a top corewrap sheet 103. The top corewrap sheet 103 may be bonded to the bottom corewrap sheet 101 by adhesive seam-beads 106. Although the top corewrap sheet 103 is shown as generally wrapping around the body 54 to bond with the bottom corewrap sheet 101, other embodiments may comprise different configurations of the bottom corewrap sheet 101 and the top corewrap sheet 103. For instance, in some embodiments, both of the bottom corewrap sheet 101 and the top corewrap sheet 103 may wrap partially around the body 54, or the bottom corewrap sheet 101 may wrap around the majority of the body 54 to bond with the top corewrap sheet 103. In still other embodiments, the body 54 may only comprise a single corewrap sheet. In such embodiments, the single corewrap sheet may wrap around the body 54 and be bonded to itself by a is single adhesive seam-bead 106. In still further of these embodiments, instead of being bonded to itself, the single corewrap sheet may wrap around the body 54, but there may be a gap between ends of the corewrap sheet thereby leaving a portion of the body 54 uncovered by the single corewrap sheet (sometimes termed a C-fold).

The bottom corewrap sheet 101 and the top corewrap sheet 103 may be formed of any suitable materials. At least the top corewrap sheet 103 may be liquid permeable and may perform well in the uptake and wicking of fluid. In some embodiments, the bottom corewrap sheet 101 may also be liquid permeable and perform well in the uptake and wicking of fluid. Although, in other embodiments, the bottom corewrap sheet 101 may be liquid impermeable to help prevent liquid from leaking out of the body 54 and/or garment 20.

The corewrap sheets 101 and/or 103 may include natural and synthetic fibers such as, but not limited to, polyester, polypropylene, acetate, nylon, polymeric materials, cellulosic materials and combinations thereof. In various embodiments, the fluid transfer layer 84 can be hydrophilic. In various embodiments, the corewrap sheets 101 and/or 103 can be hydrophobic and can be treated in any manner known in the art to be made hydrophilic. A few exemplary suitable materials comprise tissue materials, spunbond and/or meltblown materials (e.g. spunbond-meltblown materials and spunbond-meltblown-spunbond materials), spunlace materials, HYDROKNIT® materials, which are a class of materials commercially available from Kimberly-Clark World Wide, Inc., airlaid materials, and coform materials. More specifically, the corewrap sheets 101, 103 may be comprised of tissue materials having a basis weight of between about 10 gsm and about 30 gsm, spunlace materials having a basis weight of between about 20 gsm and about 50 gsm, Hydroknit® materials having a basis weight of between about 20 gsm and about 50 gsm, airlaid materials having a basis weight of between about 30 gsm and about 50 gsm, and coform materials having a basis weight of between about 35 gsm and about 60 gsm. Although, these are just some examples. Other suitable materials and/or materials having basis weights different than the above identified ranges may be used in other embodiments. For example, any suitable material known to one skilled in the art may be used, and the basis weight of any materials used for the corewrap sheets 101, 103 may be in the range of about 6 gsm to about 60 gsm.

The absorbent body 54 may be structured into a number of layers, such as layers 120, 122, and/or 124. The layer 120 may be an absorbent layer and may comprise at least a portion of a first absorbent region 132 of the body 54. The layer 122 may comprise a reinforcing material 116 disposed within the absorbent body 54 and in some embodiments may also comprise a portion of the first absorbent region 132. The layer 124 may be a second absorbent layer and may comprise at is least a portion of a second absorbent region 134 of the absorbent body 54. These different layers 120, 122, and 124 are described in more detail below.

The layer 120 may contain absorbent material to provide the absorbent body 54 with beneficial fluid uptake and storage qualities. In some embodiments, the layer 120 may be comprised substantially only of absorbent material, and substantially only of SAM in further embodiments. In the present disclosure, the phrase "substantially only" means that the described material may comprise greater than or equal to 90% of the total weight of all of the material of the layer or region. Accordingly, in the present embodiment, the layer 120 may comprise absorbent material which, when combined together, equals greater than or equal to 90% of the total weight of all of the material within the layer 120. Where the layer 120 comprises substantially only SAM, the layer 120 may comprise an amount of SAM weighing greater than or equal to 90% of the total weight of all of the material of the layer 120. In the example of FIG. 3, the layer 120 is depicted as comprising SAM particles 115, but in other embodiments the layer 120 may also comprise fibrous absorbent material, such as pulp fluff the like.

The absorbent body 54 may comprise an adhesive layer 105 disposed between the bottom corewrap sheet 101 and the layer 120. This adhesive layer 105 may help to stabilize the absorbent material in the layer 120. That is, the adhesive layer 105 may help to maintain the absorbent material within the layer 120 in position within the body 54. The adhesive layer 105 may be applied according to any suitable adhesive application method known in the art such as through a spray or a slot coat or the like. Additionally, the adhesive layer may be applied according to any suitable adhesive pattern. For example, the adhesive within the adhesive layer 105 may be applied as lines, swirls, spirals, dots, as a mesh, or as any other suitable pattern. The adhesive of adhesive layer 105 may be applied at a density of between about 1.0 g/m$^2$ and about 7.0 g/m$^2$, or between about 2.0 g/m$^2$ and about 6.0 g/m$^2$, or between about 3.0 g/m$^2$ and about 5.0 g/m$^2$, or between about 3.0 g/m$^2$ and about 4.0 g/m$^2$, or between about 3.15 g/m$^2$ and about 3.85 g/m$^2$, or between about 3.25 g/m$^2$ and about 3.75 g/m$^2$, or between about 3.4 g/m$^2$ and about 3.6 g/m$^2$, or at any other suitable density.

The layer 122 is disposed adjacent the layer 120, and may be disposed directly adjacent the layer 120 with no material in between the layers 120, 122 (such as an adhesive layer). In further embodiments, however, there may be an adhesive layer disposed between the layers 120, 122. In general, the layer 122 may comprise one or more reinforcing materials. In some embodiments, such as that shown in FIG. 3, the reinforcing material 116 may comprise a non-woven material comprised of multiple individual fibers 117, such as a spunbond material or a spunbond-meltblown-spunbond (SMS) material. In other embodiments, the nonwoven material may be a porous nonwoven material is such as a through-air bonded carded web (TABCW) or chemically bonded nonwoven materials or the like. The reinforcing material 116 may have a basis weight between about 30 gsm to about 120 gsm, or between about 35 gsm to about 110 gsm, or between about 40 gsm to about 100 gsm, or between about 40 gsm to about 90 gsm, or between about 40 gsm to about 75 gsm, or any other suitable basis weight.

In some embodiments, the layer 122 may additionally include embedded absorbent material. As used herein, the fibers 117 of the reinforcing material 116 are not considered absorbent material, regardless of the absorbent properties of the fibers 117. For instance, in the embodiment of FIG. 3 the layer 122 comprises embedded SAM particles 115. These SAM particles 115 may be disposed throughout the reinforcing material 116 of the layer 122 and trapped by the fibers 117, thereby helping to stabilize the particles 115 within the reinforcing material 116.

In embodiments where the layer 122 comprises both a reinforcing material 116 and absorbent material (such as SAM particles 115), the layers 120 and 122 may both form the first absorbent region 132 of the body 54. In total, the amount of absorbent material within the first absorbent region 132 may be between about 4 grams and about 12 grams. For instance, where the absorbent material disposed within the layers 120, 122 comprises SAM particles 115, the total weight of the SAM particles 115 disposed throughout the layer 120 and the layer 122 may be between about 4 grams and about 12 grams. Of course, the absorbent material in the layers 120, 122 does not need to be comprised solely of SAM particles 115 in all embodiments. In further embodiments, the amount of absorbent material disposed throughout the layers 120, 122 may be between about 5 grams and about 11 grams, or between about 6 grams and about 10 grams, or between about 7 grams and about 9 grams.

In some particular embodiments, the amount of absorbent material, by weight, disposed within the layer 122 may be greater or less than the amount of absorbent material in the layer 120. For instance, in some embodiments, the amount of absorbent material, by weight, in the layer 122 may comprise between about 30% and about 70% of the total amount of absorbent material within the first absorbent region 132 (e.g. layers 120 and 122). In further embodiments, the amount of absorbent material, by weight, in the layer 122 may between about 40% and about 70%, or between about 50% and about 70%, or between about 60% and about 70% of the total amount of absorbent material within the first absorbent region 132.

In order to determine the amount of absorbent material in the different layers of the absorbent body 54, the body 54 may be deconstructed in the following manner. First, the layers 122 and 124 may be removed from the layer 120. For instance, any bonds between the bottom corewrap sheet and the top corewrap sheet 103 may be broken, and the layers 122 and 124, along with the top corewrap sheet 103 may be pulled from the layer 120. This will leave the bottom corewrap sheet 101, including the adhesive layer 105 and the layer 120 separate from the rest of the layers. Since the size and basis weight of the corewrap sheet 103 is known, a total weight of the corewrap sheet may be determined from this information. Likewise, the amount, by weight, of adhesive within adhesive layer 105 is known through process parameters used for applying the adhesive in the adhesive layer 105. Accordingly, the total amount of absorbent material, by weight, in layer 120 may be determined by weighing the bottom corewrap sheet 101, including the adhesive layer 105 and the layer 120, and subtracting the weight of the corewrap sheet 101 and the adhesive in the adhesive layer 105.

To determine the amount of absorbent material embedded within the reinforcement layer 116, the reinforcement layer 116 may be removed from the top corewrap sheet 103 and the layer 124 and weighed. For instance, the reinforcement layer 116 may simply be carefully torn away from the adhesive layer 107. In such embodiments, this step can be performed over a basin to catch any loose embedded absorbent material which falls out during the tearing. Alternatively, one or more steps can be taken to deactivate the adhesive in the adhesive layer 107 to allow for easier removal of the reinforcement layer 116, for example by use of adhesive releaser or other methods known in the art. The reinforcement layer 116 may then be weighed, along with any caught loose absorbent material, to determine the overall weight of the reinforcement layer 116 and the embedded absorbent material. Since the size and basis weight of the reinforcement layer 116 is known, the total weight of the absorbent material embedded within the reinforcement layer 116 may be determined by subtracting the weight of the reinforcement layer 116 from the measured weight.

The amount of absorbent material disposed within the layer 124 may likewise be determined. For example, the top corewrap sheet 103 may be removed by breaking any bonds with the bottom corewrap sheet 101. The top corewrap sheet 103 may then be peeled away exposing the layer 124. The absorbent material within the layer 124 may be collected into a measuring basin, which can then be weighed to determine the total amount of absorbent material within the layer 124. Further steps common in the art may be taken to separate any fibrous absorbent material from the particulate absorbent material to determine the individual weights of any these individual components. Any of the recited percentages of absorbent material, either within a given layer 120, 122, and 124, or between any of the layers 120, 122, and 124 may be readily determined after determining the appropriate absolute weights.

The layer 124 may represent another absorbent layer comprising absorbent material. As seen in FIGS. 3-12, the layer 124 is disposed between the top corewrap sheet 103 and the reinforcing material 116. The layer 124 may also form the second absorbent region 134. In some embodiments, the layer 124 may comprise substantially only fibrous absorbent material, such as absorbent fibers 113, and in some specific embodiments may be comprised 100% of fibrous absorbent material. In other embodiments, the layer 124 may comprise substantially only superabsorbent material, such as SAM particles 111, and in some more specific embodiments may be comprised 100% of superabsorbent material. In still further embodiments, the layer 124 may comprise a mixture of both absorbent fibers 113 and SAM particles 111, as in FIGS. 3-12. In at least some of these embodiments, the SAM particles 111 and the absorbent fibers 113 may be disposed such that the layer 124 represents a relatively uniform mixture of the SAM particles 111 and the fibers 113.

Where the layer 124 comprises both SAM particles 111 and absorbent fibers 113, the layer 124 may contain differing amounts of SAM particles 111 and absorbent fibers 113 in different embodiments. For example, the layer 124 may comprise anywhere between about 5% and about 95%, by weight, of superabsorbent material. That is, of the total weight of the material which comprises the layer 124, the superabsorbent material may comprise anywhere between about 5% and about 95% of that total weight. In further embodiments, the layer 124 may comprise anywhere between about 10% and about 90%, by weight, of superabsorbent material, or anywhere between about 20% and about 90%, by weight, of superabsorbent material, or anywhere between about 30% and about 90%, by weight, of superabsorbent material, or anywhere between about 40% and about 90%, by weight, of superabsorbent material, or anywhere between about 50% and about 90%, by weight, of superabsorbent material, or anywhere between about 50% and about 85%, by weight, of superabsorbent material, or anywhere between about 50% and about 80%, by weight, of superabsorbent material, or anywhere between about 60% and about 80%, by weight, of superabsorbent material. In such embodiments where the layer 124 is comprised 100% of absorbent material, the remainder of the weight of the layer 124 may be comprised of fibrous absorbent material.

In absolute weights, the amount of superabsorbent material in the layer 124 may be between about 0 g and about 20 g, or between about 0 g and about 15 g, or between about 0 g and about 10 g, or between about 0 g and about 8 g, or between about 2 g and about 8 g, or between about 3 g and about 8 g, or between about 3 g and about 6 g, or between about 3 g and about 5 g. The absolute weight of fibrous absorbent material in the layer 124 may be between about 0 g and about 20 g, or between about 0 g and about 15 g, or between about 0 g and about 10 g, or between about 0 g and about 8 g, or between about 2 g and about 8 g, or between about 2 g and about 6 g, or between about 2 g and about 5 g.

Another feature of the body 54 may be the relation of the amount of absorbent material within the second absorbent region 134 to the amount of absorbent material in the first absorbent region 132. In some embodiments, the amount of absorbent material, by weight, within the second absorbent region 134 may be between about 60% and about 140% of the amount of absorbent material within the first absorbent region 132. In further embodiments, the amount of absorbent material, by weight, within the second absorbent region 134 may be between about 70% and about 130%, or between about 75% and about 125%, or between about 75% and about 115%, or between about 75% and about 110%, of the amount of absorbent material within the first absorbent region 132. These percentages include all absorbent material within the regions 132, 134.

Another aspect of the body 54 may be the relation of the amount of superabsorbent material within the second absorbent region 134 to the amount of superabsorbent material in the first absorbent region 132. In some embodiments, the amount of superabsorbent material, by weight, within the second absorbent region 134 may be between about 30% and about 70% of the amount of superabsorbent material within the first absorbent region 132. In further embodiments, the amount of superabsorbent material, by weight, within the second absorbent region 134 may be between about 35% and about 65%, or between about 35% and about 60%, or between about 40% and about 60%, of the amount of superabsorbent material within the first absorbent region 132.

In some particular embodiments, a single type of SAM may be used throughout all of the absorbent layers of the body 54. For instance, a type of SAM having the following properties may be used in some embodiments in layers 120, 122, and/or 124. Test Methods used in identifying the properties of SAM are disclosed herein further below.

TABLE 1

| SAM type | CRC (g/g) | Absorbency Under Load (g/g) | Free Swell Gel Bed Permeability (Darcy) | Vortex (Seconds) |
|---|---|---|---|---|
| A | Between about 25-40 | Greater than about 10 | Between about 10-80 | Between about 20-70 |

In other embodiments, two different types of SAM may be mixed together and used in layers 120, 122, and/or 124. Table 2 below details two particular types of SAM and their properties which may exhibit positive performance results when mixed together and used in absorbent bodies 54 of the present disclosure.

TABLE 2

| SAM type | CRC (g/g) | Absorbent Under Load (g/g) | Free Swell Gel Bed Permeability (Darcy) | Vortex (Sec) |
|---|---|---|---|---|
| B | Between about 25-40 | Greater than about 10 | Between about 10-70 | Between about 30-70 |
| C | Between about 25-40 | Greater than about 10 | Between about 15-80 | Between about 20-60 |

Table 3 details additional exemplary types of SAM and their properties which may exhibit positive performance results when used in absorbent bodies 54 of the present disclosures as a mixture for use in layers 120, 122, and/or 124.

TABLE 3

| SAM type | CRC (g/g) | Absorbent Under Load (g/g) | Free Swell Gel Bed Permeability (Darcy) | Vortex (Sec) |
|---|---|---|---|---|
| D | Between about 28-43 | Greater than about 10 | Between about 5-50 | Between about 20-50 |
| E | Between about 28-43 | Greater than about 10 | Between about 10-60 | Between about 15-45 |

In still further embodiments, absorbent bodies 54 of the present disclosure may comprise any single one of the SAM types A, B, C, D, or E or a mixture of any of the SAM types A, B, C, D, and/or E. For example, in some embodiments, the layers 120, 122 may comprise any one of the described SAM types A, B, C, D, or E. In the same embodiments, the layer 124 may comprise the same SAM type or any other one of the SAM types A, B, C, D, and E. In other embodiments, the layers 120, 122 may comprise a mixture of any two of the SAM types A, B, C, D, and E. In these embodiments, the layer 124 may comprise any one of the SAM types A, B, C, D, or E or a mixture of any two of the SAM type A, B, C, D, and E. In still other embodiments, the layers 120, 122 may comprise any one of the SAM types A, B, C, D, or E while the layer 124 comprises any two of the SAM types A, B, C, D, and E. In particular embodiments, the layers 120, 122, and 124 may all comprise the SAM type A. In further embodiments, the layers 120, 122 may comprise a mixture of the SAM types D and E while the layer 126 comprises any one of the SAM types A, B, C, D, or E. Alternatively, the layer 126 may comprise a mixture of the SAME types B and C in such embodiments.

The body 54 may further comprise adhesive layers 107 and 109. The adhesive layer 107 may be disposed between the reinforcing material 116 and the layer 124. The adhesive layer 109 may be disposed between the layer 124 and the top corewrap sheet 103. In general, these adhesive layers 107, 109 may be similar to the adhesive layer 105, in terms of the amount and/or density of adhesive and the types of adhesives, for example.

Figure 4:
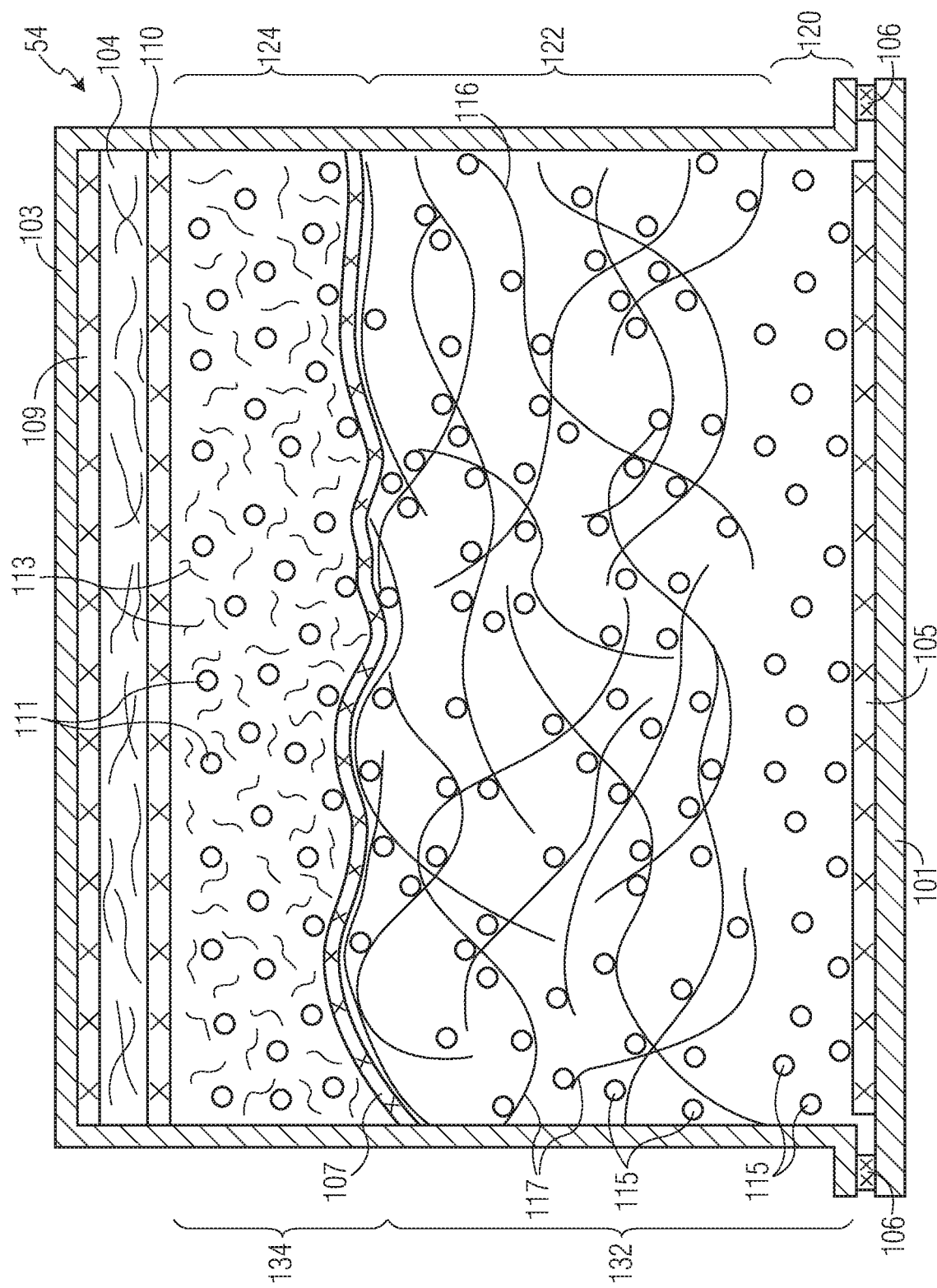
FIG. 4 is cross-section of another exemplary absorbent body for use in an absorbent article, according to aspects of the present disclosure.
Figure 5:
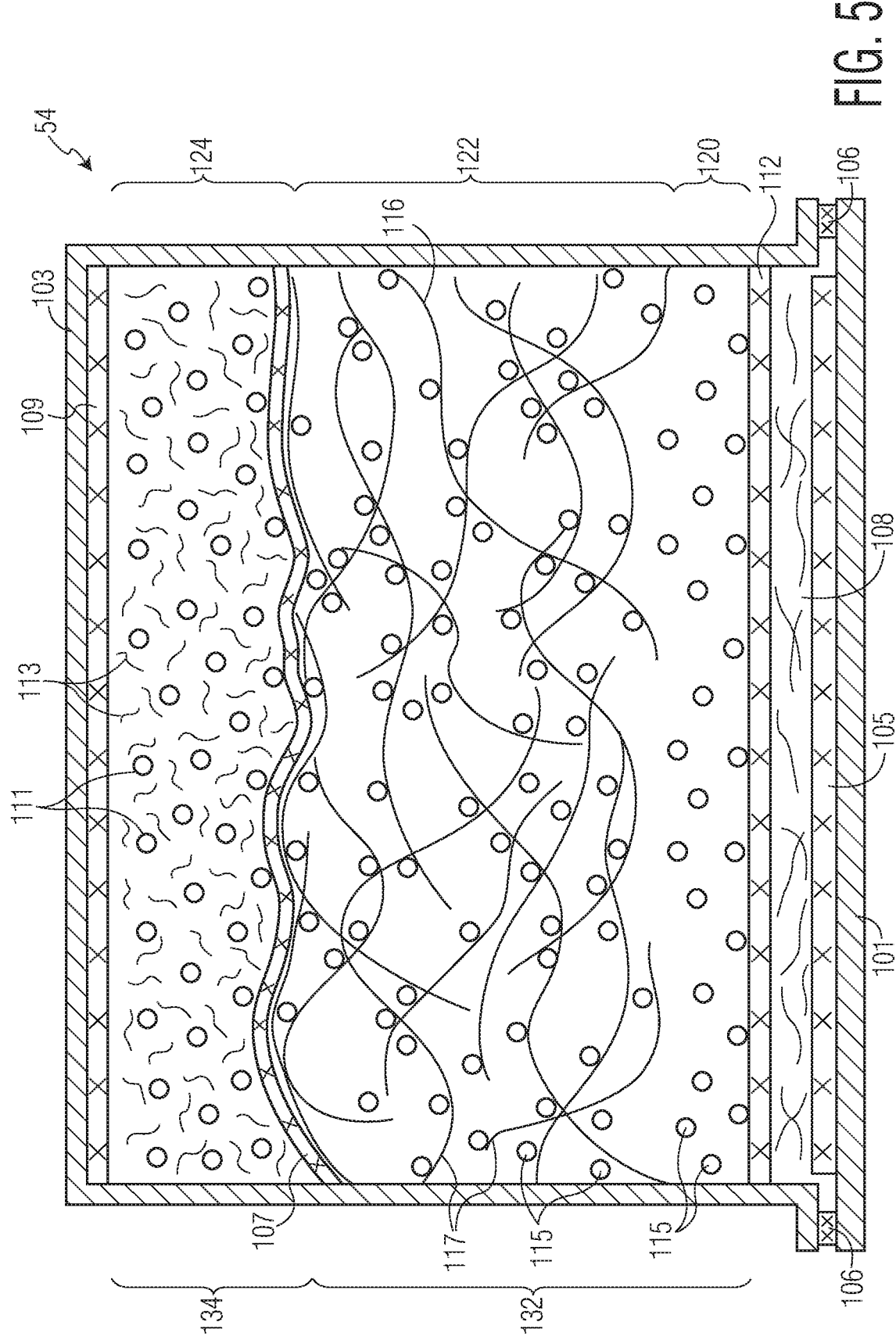
FIG. 5 is a cross-section of yet another exemplary absorbent body for use in an absorbent article, according to aspects of the present disclosure.
Figure 6:
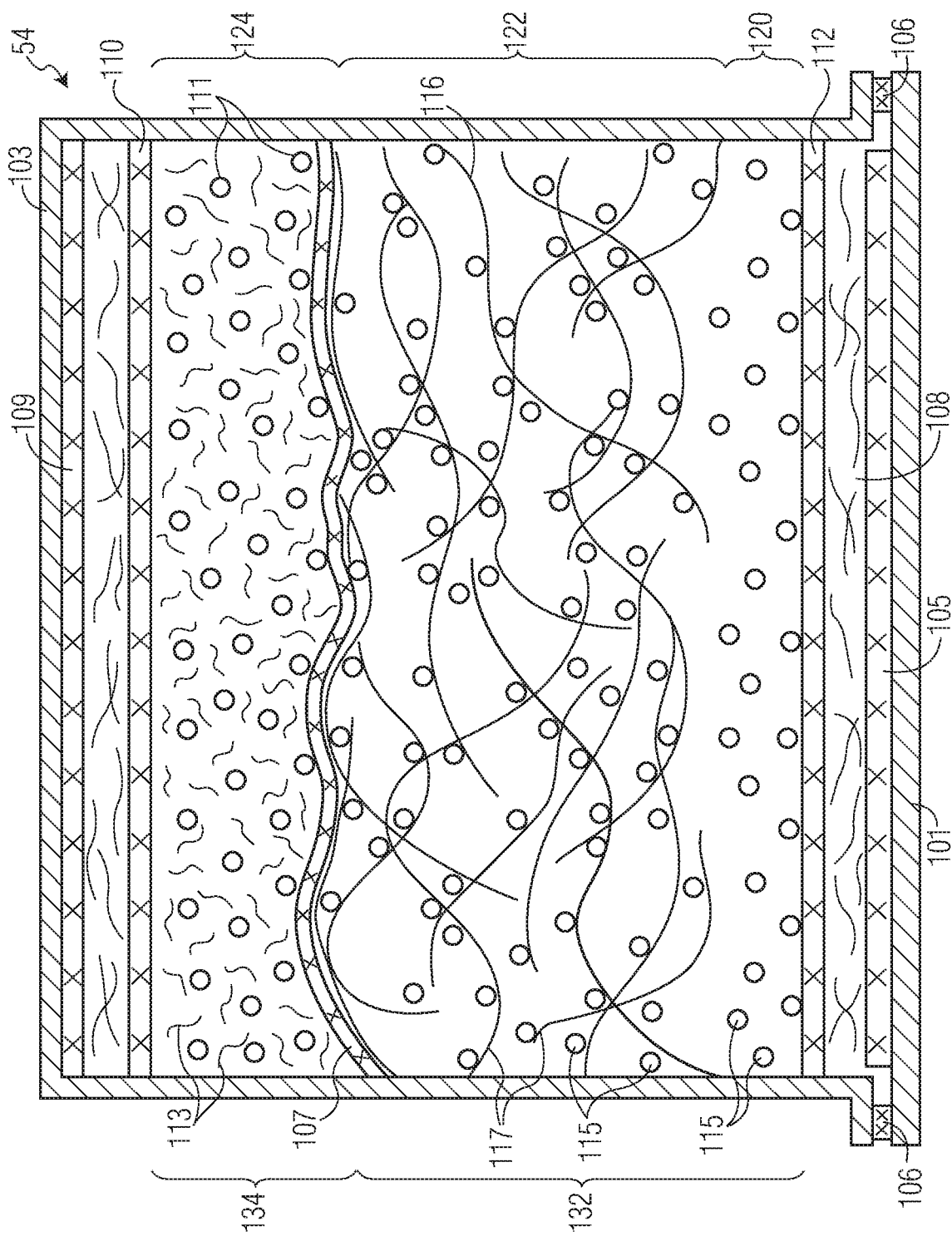
FIG. 6 is a cross-section of yet another exemplary absorbent body for use in an absorbent article, according to aspects of the present disclosure.

FIGS. 4-6 are additional exemplary cross-sections of the body 54 as viewed along line 3-3 in FIG. 2, according to additional aspects of the present disclosure. The absorbent bodies 54 depicted in FIGS. 3-5 may be generally similar to those described with respect to FIG. 3. However, the absorbent bodies 54 in the embodiments of FIGS. 3-5 may include one or more additional layers. For example, the body 54 may further comprise one or more fibrous material layers 104 and/or 108 disposed adjacent the top corewrap sheet 103 and/or the bottom corewrap sheet 101, respectively. Where included, the fibrous material layers 104 and/or 108 may comprise any nonwoven material, such as any of those described with respect to the corewrap sheets 101, 103. In some specific embodiments, the fibrous material layers 104 and/or 108 may comprise an airlaid material. Such airlaid materials may have basis weights that range between about 40 gsm and about 60 gsm, or between about 45 gsm and about 55 gsm. As can be seen in FIGS. 3-5, embodiments where the body 54 comprises one or more of the material layers 104 and/or 108, the body 54 further comprises additional adhesive layers 110 and/or 112 disposed adjacent the layers 104 and/or 108, with the layers 104 and/or 108 disposed between the additional adhesive layers 110 and/or 112 and the top corewrap sheet 103 or the bottom corewrap sheet 101. These adhesive layers 110 and/or 112 may be similar to the other adhesive layers 105, 107, and/or 109, for example in terms of the amount and/or density of adhesive and the types of adhesives.

Figure 7:
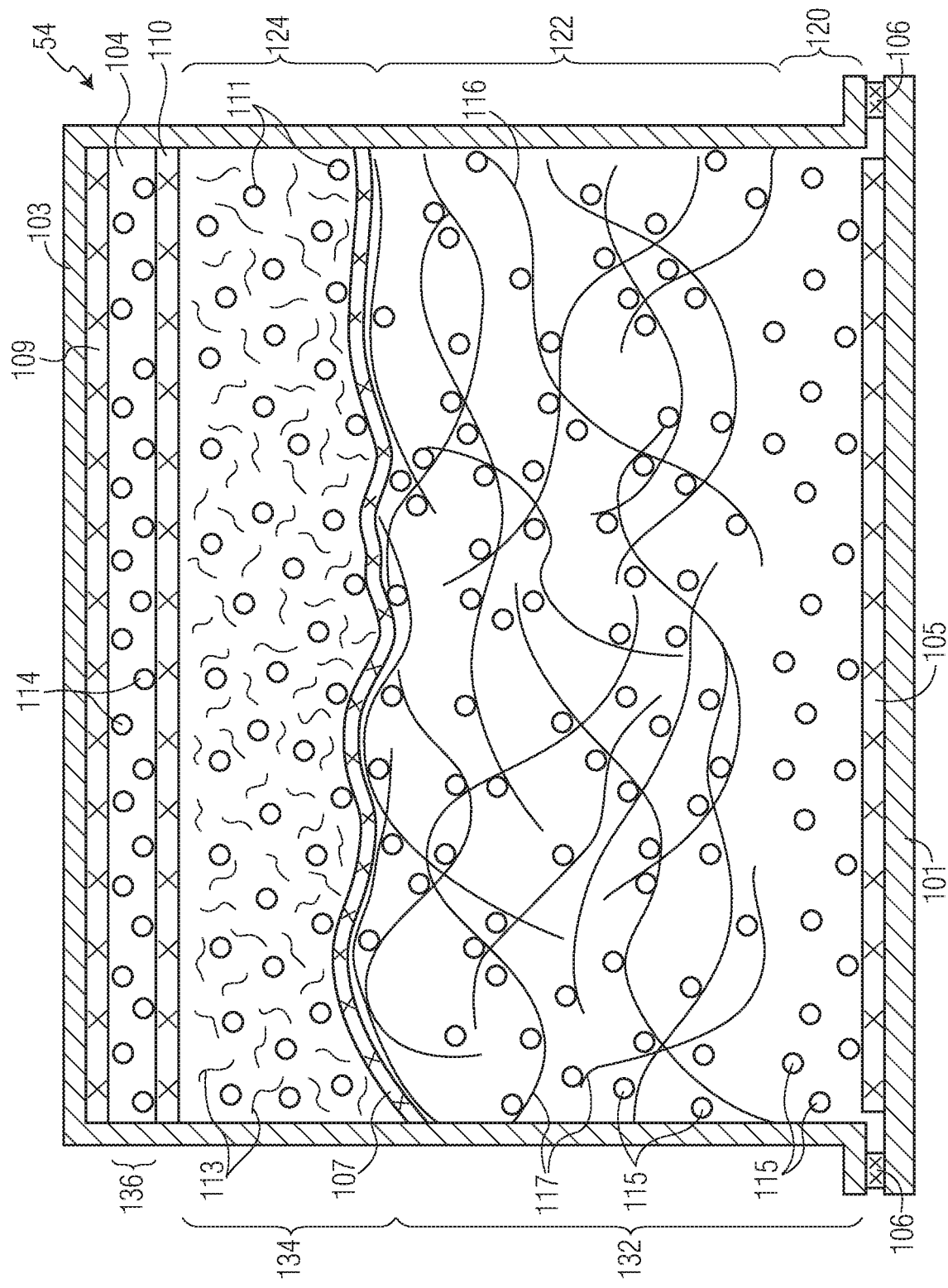
FIG. 7 is a cross-section of yet another exemplary absorbent body for use in an absorbent article, according to aspects of the present disclosure.

FIGS. 7-10 are cross-sections of the absorbent body 54 as viewed along line 3-3 of FIG. 2, according to further aspects of the present disclosure. FIG. 7 depicts an exemplary absorbent body 54 further comprising layer 126. The layer 126 may be yet another absorbent layer and may comprise a third absorbent region 136. In some embodiments, the layer 126 may comprise substantially only absorbent material, and in some specific embodiments may be comprised 100% of absorbent material. Although shown as only comprising superabsorbent particles 114, the layer 126 may comprise only fibrous absorbent material in other embodiments, and a mixture of both superabsorbent material and fibrous absorbent material in further embodiments.

The amount of absorbent material disposed within the layer 126 comprising the third absorbent region 136 may comprise between about 10% and about 40%, by weight, of the amount of absorbent material disposed within the first absorbent region 132 and the second absorbent region 134. For example, if the amount of absorbent material disposed within the first absorbent region 132 is 8 g and the amount of absorbent material disposed within the second absorbent region 134 is 7 g, than the amount of absorbent material disposed within the third absorbent region 136 may be between about 10% and about 40% of 15 g (e.g. between about 1.5 g and about 6 g). In further embodiments, however, the amount of absorbent material disposed within the third absorbent region 136 may comprise between about 12.5% and about 35%, or between about 15% and about 30%, or between about 17.5% and about 25%, by weight, of the amount of absorbent material disposed within the first absorbent region 132 and the second absorbent region 134.

Figure 8:
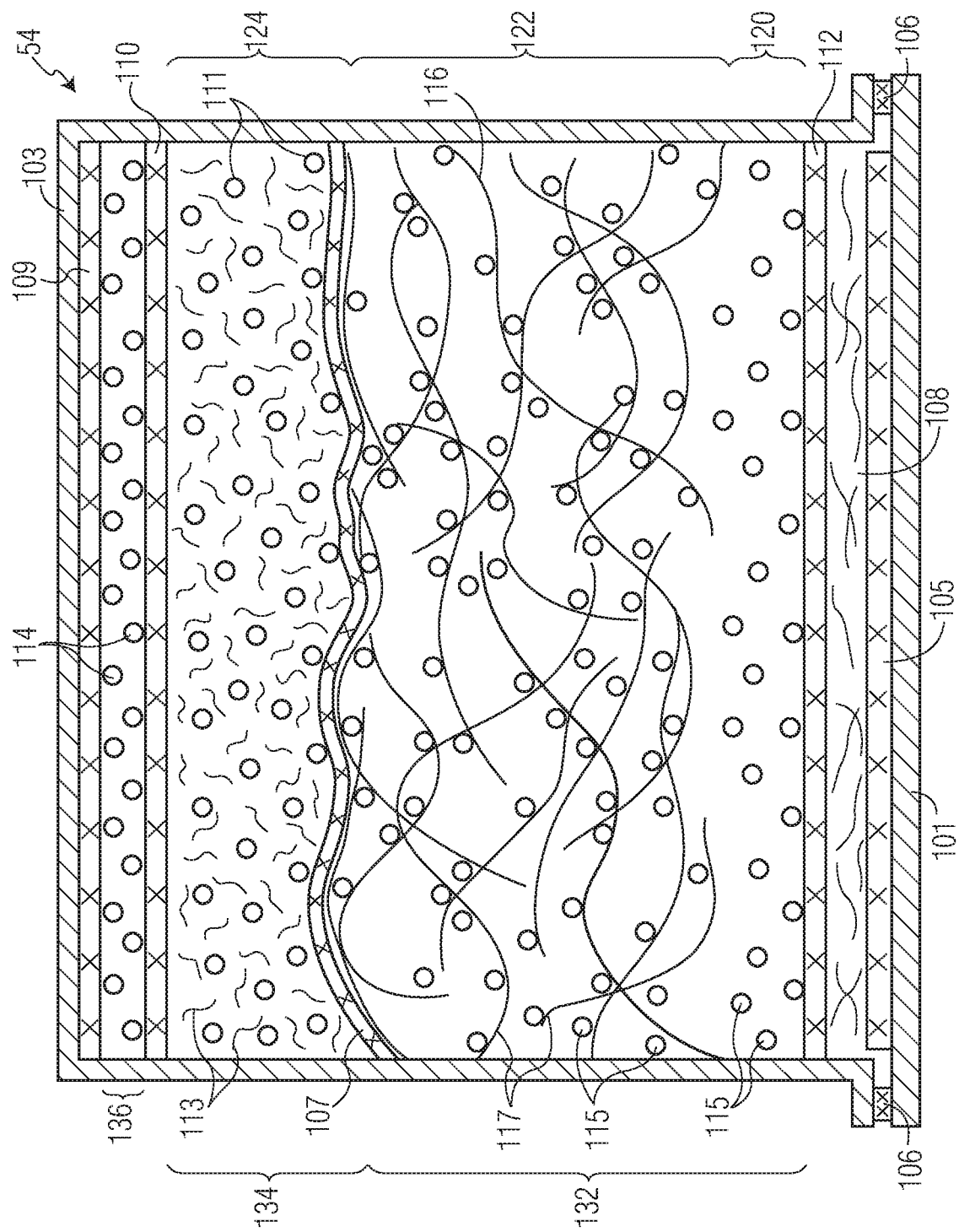
FIG. 8 is a cross-section of yet another exemplary absorbent body for use in an absorbent article, according to aspects of the present disclosure.
Figure 9:
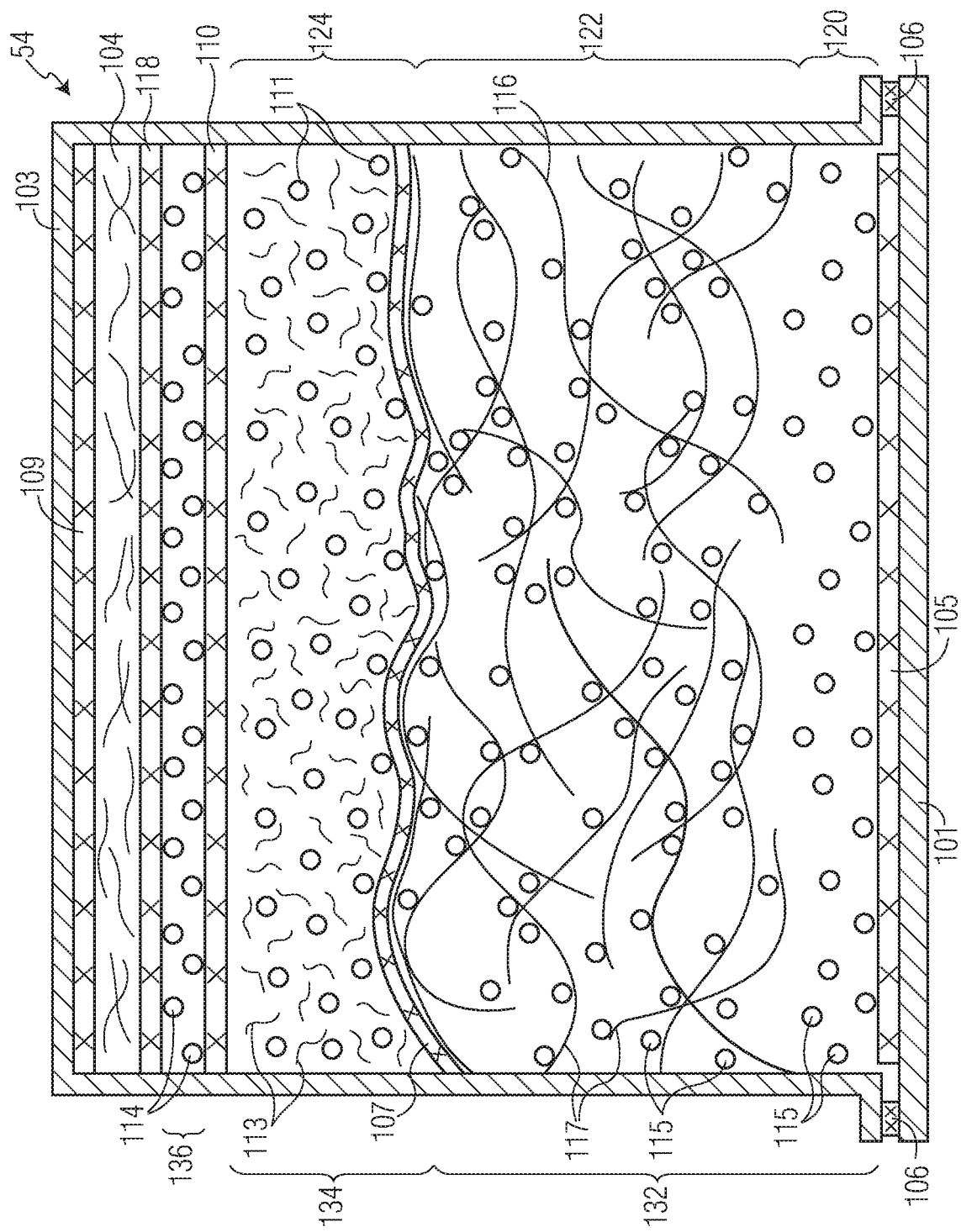
FIG. 9 is a cross-section of yet another exemplary absorbent body for use in an absorbent article, according to aspects of the present disclosure.
Figure 10:
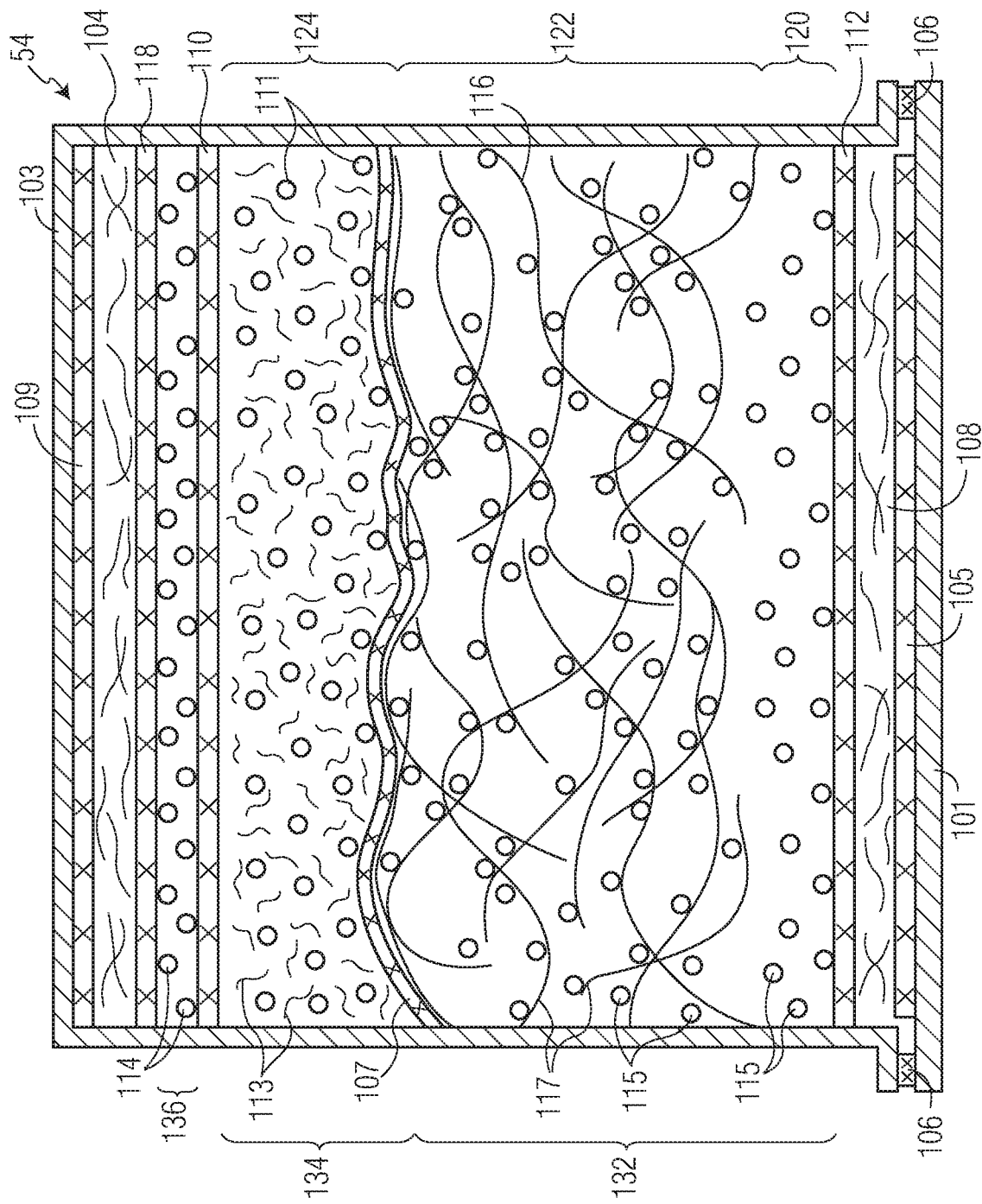
FIG. 10 is a cross-section of yet another exemplary absorbent body for use in an absorbent article, according to aspects of the present disclosure.

The FIGS. 8-10 illustrate further embodiments of the absorbent body 54 which include the layer 126 and one or more additional fibrous material layers 104 and/or 108. For instance, FIG. 8 depicts an embodiment where the absorbent body 54 comprises both the layer 126 and the bottom fibrous material layer 108. FIG. 9 depicts an embodiment where the absorbent body 54 comprises both the layer 126 and the top fibrous material layer 104. FIG. 10 depicts an embodiment where the absorbent body 54 comprises all of the layer 126, the top fibrous material layer 104, and the fibrous bottom material layer 108. In the embodiments of FIGS. 9 and 10, an additional adhesive layer, adhesive layer 118, is further depicted. This additional adhesive layer 118 is disposed between layer 126 and the top fibrous material layer 104, while the adhesive layer 110 separates the layer 126 and the absorbent layer 124 comprising the reinforcing material 116 in these embodiments.

Figure 11:
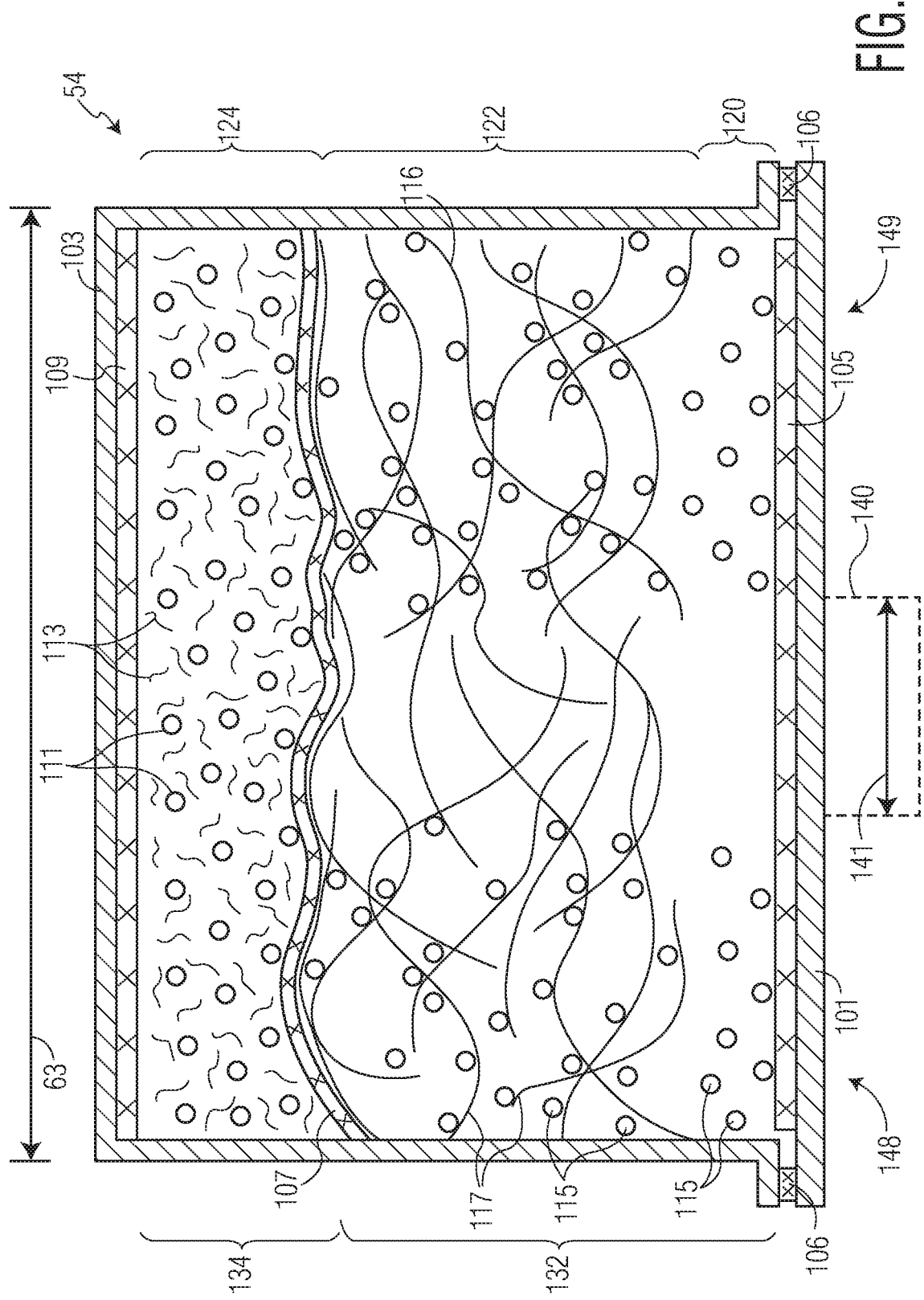
FIG. 11 is a cross-section of yet another exemplary absorbent body for use in an absorbent article, according to aspects of the present disclosure.
Figure 12:
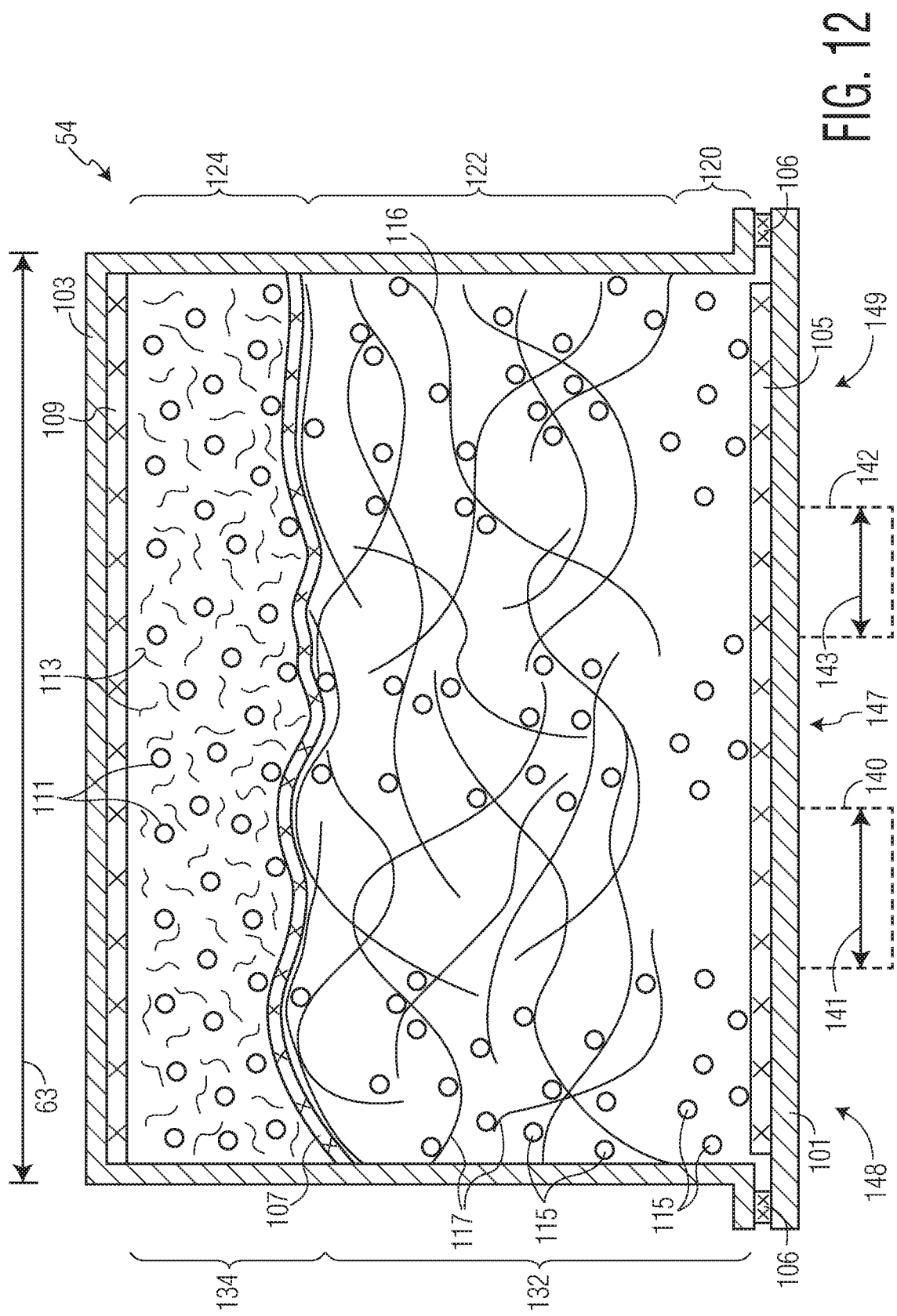
FIG. 12 is a cross-section of yet another exemplary absorbent body for use in an absorbent article, according to aspects of the present disclosure.

FIGS. 11 and 12 are cross-sections of the absorbent body 54 as viewed along line 3-3 of FIG. 2 depicting still further embodiments according to the present disclosure. In the embodiment of FIG. 11, the absorbent body 54 comprises a channel 140 having a lower absorbent material content than surrounding regions, such as regions 148 and 149. It should be understood that the regions 148, 149 correspond to regions of the absorbent body 54 disposed within the same layer or layers as the channel 140. If the channel 140 is disposed only within the layer 122, than the regions 148, 149 correspond to regions of the layer 122. Where the channel 140 is disposed through both of the layers 122 and 124, then the regions 148, 149 correspond to regions extending through both of the layers 122, 124. The channel 140 is further shown in FIG. 11 as extending through both of the layers 122, 124. However, in some embodiments, the channel 140 may only extend through the layer 122.

As shown, the channel 140 may have a channel width 141 that extends in the lateral direction 22. In some embodiments, the channel width 141 may be between about 5% and about 40% of the overall absorbent body width 63. In further embodiments, the channel width 141 may be between about 5% and about 35%, or be between about 5% and about 30%, or be between about 5% and about 25%, or be between about 5% and about 20%, or be between about 5% and about 15%, or be between about 5% and about 10% of the overall absorbent body width 63.

The channel 140 may further have a longitudinal length (not shown) which extends in the longitudinal direction 23. In some embodiments, the longitudinal length of the channel 140 may equal a longitudinal length 61 of the absorbent body 54. However, in other embodiments, the longitudinal length of the channel 140 may only be between about 25% to about 90% of the longitudinal length 61 of the absorbent body 54. In still further embodiments, the longitudinal length of the channel 140 may be between about 25% and about 80%, or between about 30% and about 80%, or between about 30% and about 75%, or between about 30% and about 70%, or between about 35% and about 65% of the longitudinal length 61 of the absorbent body 54.

In particular embodiments, there may be substantially no absorbent material disposed within the channel 140. In other embodiments, however, the channel 140 may have a relatively lesser amount of absorbent material disposed within the channel 140 than in the regions outside of the channel, e.g. the regions 148, 149. For example, the amount of absorbent material within the channel 140 may be between about 0.5% and about 10%, by weight, of the amount of absorbent material disposed within the regions 148, 149. As one example, channel 140 extends through both of the layers 120 and 122, and each of the regions 148, 149 comprises absorbent material having a combined weight of 7 g, then the total amount of absorbent material disposed within the channel 140 may be between about 0.035 g and about 0.7 g.

FIG. 12 depicts a further example embodiment of the absorbent body 54 including both a first channel 140 and a second channel 144, and a further central region 147. In general, the second channel 144 may be similar in any respect to those features described above for the channel 140. As one example, the second channel 144 may have a second channel width 145, and the second channel 145 may be similar to the widths described with respect to channel width 144. Additionally, the amount of any absorbent material disposed within the second channel 144 may be similar to that described with respect to the channel 140.

Figure 13:
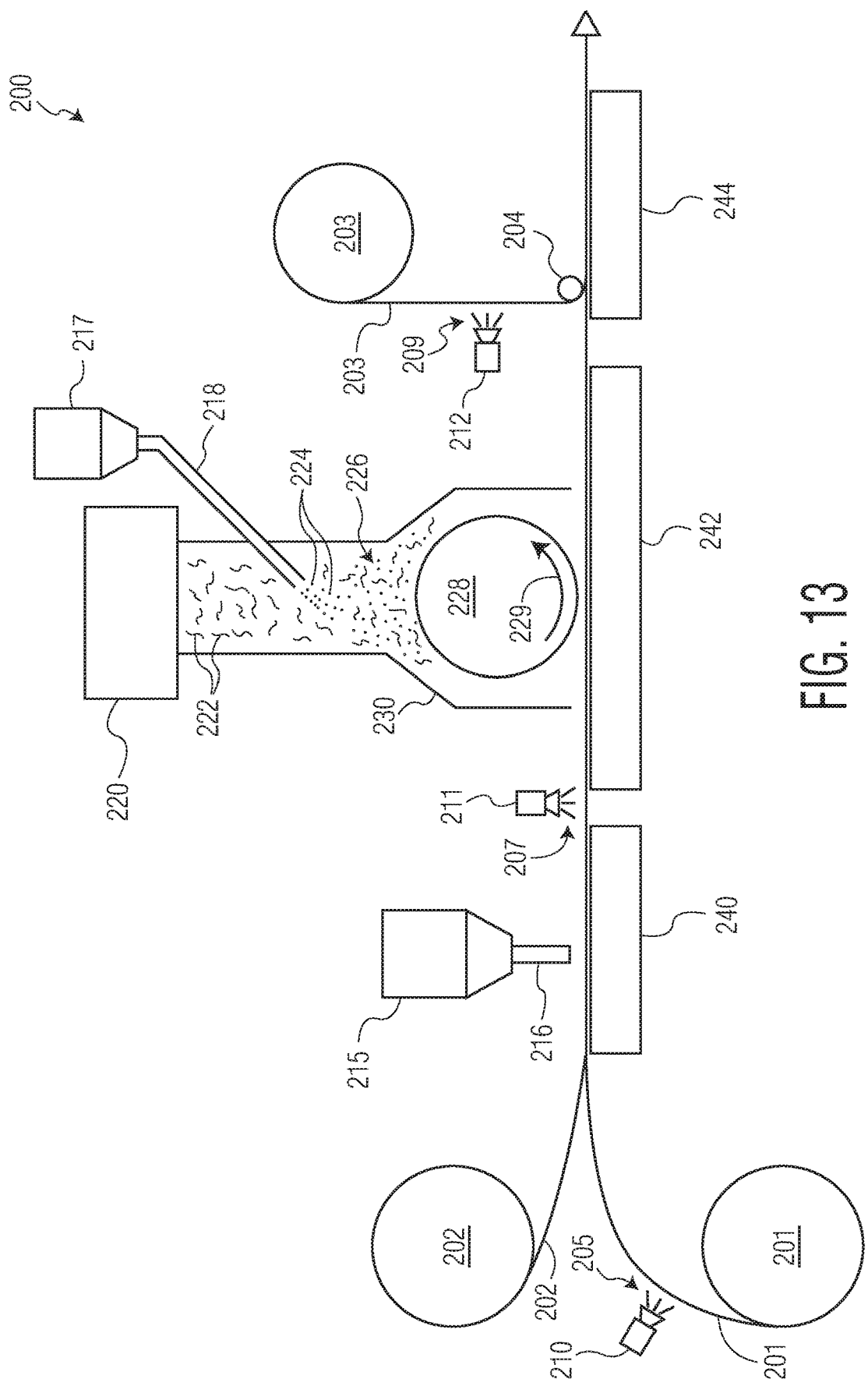
FIG. 13 is a schematic depiction of an exemplary method for forming absorbent bodies of the present disclosure.

FIG. 13 is a schematic depiction of a method 200 of manufacturing the absorbent bodies 54 of the present disclosure. In a first step, a bottom corewrap sheet 201 may be unwound from a spool of material. The bottom corewrap sheet 201 may correspond to the bottom corewrap sheet 101 is described previously with respect to the absorbent bodies 54 of the present disclosure. A first adhesive 205 may be applied to the bottom corewrap sheet 201 by adhesive applicator 210 forming a first adhesive layer on the bottom corewrap sheet 201. The adhesive 205 forming the first adhesive layer may correspond to the adhesive 105 described previously. For instance, adhesive 205 may be applied in any manner, pattern, and/or basis weights described with respect to the adhesive 105.

A reinforcing material 202 may also be unwound from a spool and may further be coupled to the bottom corewrap sheet 201, with the adhesive 205 sandwiched between the bottom corewrap sheet 201 and the reinforcing material 202. The reinforcing material 202 may correspond to the reinforcing material 116 described above. Although shown as being applied to the bottom corewrap sheet 201 in FIG. 13 (and in FIG. 14), in alternative embodiments, the adhesive 205 may be applied to the reinforcing material 202 on the side of the reinforcing material 202 disposed adjacent the bottom corewrap sheet 201 when the sheet 201 and the material 202 are brought together.

Next, the combined bottom corewrap sheet 201 and reinforcing material 202 are transported to a vacuum conveyer 240, through which air is drawn through the bottom corewrap sheet 201 and the reinforcing material 202 and into the vacuum conveyer 240. While the bottom corewrap sheet 201 and the reinforcing material 202 are disposed over the vacuum conveyer 240, superabsorbent material may be dispersed over and onto the reinforcing material 202. For example, the superabsorbent material may be stored in a hopper 215 and may be dispensed through conduit 216 to the reinforcing material 202. In some embodiments, the superabsorbent material is dispensed in a metered fashion such that a designated amount of superabsorbent material is deposited onto the reinforcing material 202. In different embodiments, the amount of superabsorbent material deposited onto the reinforcing material 202 may coincide with the amount of superabsorbent material contained within the layers 120, 122 of the absorbent bodies 54 described above.

The bottom corewrap sheet 201, reinforcing material 202, and deposited superabsorbent material are then transported to a second vacuum conveyer 242—although the use of one or more vacuum conveyers should not be construed as a limiting feature of the method 200. A second adhesive 207 is then applied to the reinforcing material 202 by adhesive applicator 211, on the same side of the reinforcing material 202 to which the superabsorbent material was deposited to form a partial core assembly of the bottom corewrap sheet 201, adhesive 205, reinforcing material 202, deposited superabsorbent material, and adhesive 207. The adhesive 207 may form a second adhesive layer, which may correspond to the adhesive layer 107 described previously.

This partial core assembly is then moved through a forming chamber 230. Inside the is forming chamber 230 absorbent material is deposited onto a forming drum 228, which rotates in the direction of arrow 229. The forming drum 228 may be connected to a vacuum source drawing air through the drum, thereby helping the deposition of absorbent material onto the drum 228. The absorbent material deposited onto the forming drum 228 corresponds to the absorbent material that forms the layer 124 of the absorbent bodies 54 of the present disclosure. In the embodiment of FIG. 13, the absorbent material within the forming chamber 230 comprises both fibrous absorbent material 222 and particulate superabsorbent material 224. The fibrous absorbent material 222 is supplied by fiberizer 220, while the particulate superabsorbent material 224 is supplied by hopper 217 and is transported to the chamber 230 through the conduit 218. The amounts of fibrous absorbent material supplied by the fiberizer 220 and of particulate superabsorbent material 224 supplied by the hopper 217 to the chamber 230 may be metered so as to deposit a designated amount of the materials 222, 224 onto the forming drum 228. In different embodiments, the amounts of materials 222, 224 that are deposited onto the forming drum 228 may correspond to the amounts of fibrous and/or particulate absorbent materials disposed within the layer 124 of the absorbent bodies described previously.

Figure 14:
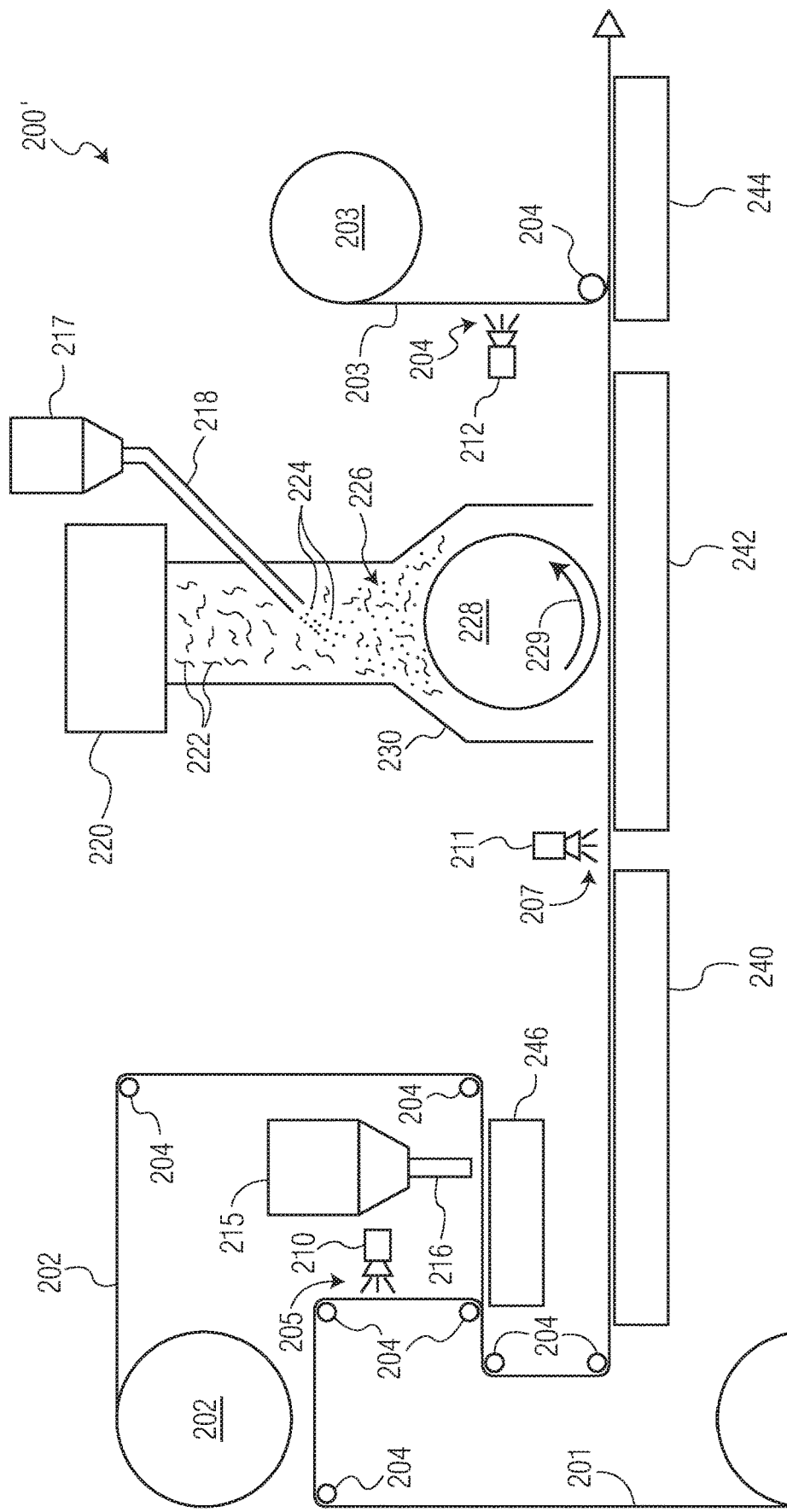
FIG. 14 is a schematic depiction of another exemplary method for forming absorbent bodies of the present disclosure.

It should be understood that although FIGS. 13 and 14 depict both fibrous absorbent material 222 and particulate superabsorbent material 224 combined and deposited onto the drum 228, in other embodiments the absorbent material deposited onto the drum 228 may comprise only one of fibrous absorbent material and particulate superabsorbent material. For instance, embodiments of absorbent bodies 54 described previously included embodiments where the layer 124 only comprised fibrous absorbent material and embodiments where the layer 124 only comprise particulate superabsorbent material. Where chamber 230 includes both fibrous absorbent material 222 and particulate superabsorbent material 224, the airflow within the forming chamber 230 may be sufficient to mix the fibrous absorbent material 222 and particulate superabsorbent material 224 together, as indicated in region 226 of the chamber 230, such that the materials 222, 224 deposit onto the drum 228 as a substantially uniform mixture.

As the surface of the forming drum 228 comes in proximity to the partial core assembly disposed on the vacuum conveyer 242, the absorbent material that was deposited onto the drum 228 is separated from the drum 228 and coupled to the adhesive 207 disposed on the reinforcing material 202. For example, the drum 228 may be designed such that airflow through the drum is blocked in the region of the drum proximate the vacuum conveyer 242. This may be enough for the deposited absorbent material to separate from the drum 228 and couple to the partial core assembly. In other embodiments, the drum 228 may blow air out through the drum surface, thereby forcing the is deposited absorbent material off of the drum surface.

Next, the partial core assembly, including the deposited absorbent material, is coupled to the top corewrap sheet 203, which may be unwound from a spool. In the embodiments of FIGS. 13 and 14, a third adhesive 209 is applied by adhesive applicator 212 to the top corewrap sheet 203 before the top corewrap sheet 203 is brought onto the partial core assembly. This third adhesive 209 may form an adhesive layer which may correspond to the adhesive layer 109. As can be seen, the third adhesive 209 is applied to the top corewrap sheet 203 such that the third adhesive is disposed between the top corewrap sheet 203 and the partial core assembly. However, in other embodiments, the third adhesive 209 may be applied directly to the partial core assembly, instead of to the top corewrap sheet 203, before the top corewrap sheet 203 is applied to the partial core assembly.

FIG. 14 is a schematic depiction of an alternative method 200' of manufacturing the absorbent bodies 54 of the present disclosure. The method 200' is similar to the method 200, except that method 200' includes applying particulate superabsorbent material to the reinforcing material 202 in a different manner. As can be seen in FIG. 13, the method 200 describes applying particulate superabsorbent material to the reinforcing layer 202 at a side disposed away from the bottom corewrap sheet 201. In contrast, the method 200' further comprises an additional vacuum conveyer 246 and web handling components 204. The method comprises moving the reinforcing layer to the vacuum conveyer 246 without the bottom corewrap sheet 201 and depositing particulate superabsorbent material onto the reinforcing layer 202 while the reinforcing layer 202 is disposed over the vacuum conveyer 246. Once the particulate superabsorbent material has been deposited onto the reinforcing layer 202, then the bottom corewrap sheet 201 and the reinforcing layer 202 are brought together. Notably, the method 200' shows applying the particulate superabsorbent material to the side of the reinforcing layer 202 that is disposed adjacent the bottom corewrap sheet 201, whereas the method 200 shows applying the particulate superabsorbent material to the side of the reinforcing layer 202 disposed away from the bottom corewrap sheet 201.

Of course, the methods 200 and/or 200' may be modified in one or more ways to incorporation application of one or more additional layers of absorbent material, web material, and/or adhesive. For instance, FIGS. 4-10 depict embodiments of absorbent body 54 where the absorbent body includes additional layers such as layers material layers 104, 108 and/or absorbent material layer 126 with one or more of adhesive layers 110, 112, 118. Accordingly, alternative contemplated methods to methods 200, 200' include application of layers 110, 112, and/or 126 with one or more of adhesive layers 110, 112, 118 as appropriate to form the described absorbent bodies 54.

Centrifuge Retention Capacity Test (CRC)

The CRC Test measures the ability of the particulate superabsorbent polymer composition to retain liquid therein after being saturated and subjected to centrifugation under controlled conditions. The resultant retention capacity is stated as grams of liquid retained per gram weight of the sample, (g/g). The CRC Test can be performed either before or after subjecting the particulate superabsorbent polymer composition to a Processing Test, as set forth herein. The sample to be tested is prepared from particles that are pre-screened through a U.S. standard 30-mesh screen and retained on a U.S. standard 50-mesh screen. As a result, the particulate superabsorbent polymer composition sample comprises particles sized in the range of about 300 to about 600 microns. The particles can be pre-screened by hand or automatically.

The retention capacity is measured by placing about 0.20 grams of the pre-screened particulate superabsorbent polymer composition sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Connecticut, U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals are about 0.25 inches inside the edge of the material. After the sample is placed in the pouch, the remaining open edge of the pouch is also heat-sealed. Empty bags are also made to serve as controls. Three samples are prepared for each particulate superabsorbent polymer composition to be tested.

The sealed bags are submerged in a pan containing the test solution at about 23° C., making sure that the bags are held down until they are completely wetted. After wetting, the particulate superabsorbent polymer composition samples remain in the solution for about 30 minutes, at which time they are removed from the solution and temporarily laid on a non-absorbent flat surface.

The wet bags are then placed into the basket wherein the wet bags are separated from each other and are placed at the outer circumferential edge of the basket, wherein the basket is of a suitable centrifuge capable of subjecting the samples to a g-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning. The bags (including the wet, empty bags) are centrifuged at is about 1,600 rpm (e.g., to achieve a target g-force of about 350 g force with a variance from about 240 to about 360 g force), for 3 minutes. G force is defined as an unit of inertial force on a body that is subjected to rapid acceleration or gravity, equal to 32 ft/sec$^2$ at sea level. The bags are removed and weighed, with the empty bags (controls) being weighed first, followed by the bags containing the particulate superabsorbent polymer composition samples. The amount of solution retained by the particulate superabsorbent polymer composition sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

$$CRC = \frac{\begin{bmatrix} \text{sample bag after centrifuge} - \\ \text{empty bag after centrifuge} - \\ \text{dry sample weight} \end{bmatrix}}{\text{dry sample weight}}$$

The three samples are tested, and the results are averaged to determine the CRC of the particulate superabsorbent polymer composition.

CRC(rt, 0.5 hr) is measured with a testing temperature of about 23° C. (room temperature) and a testing time of 0.5 hour.

CRC(bt, 5 hr) is measured with a testing temperature of about 37° C. (body temperature) and a testing time of 5 hours.

Absorbency Under Load Test (AUL(0.9 psi))

The Absorbency Under Load (AUL) Test measures the ability of the particulate superabsorbent polymer composition to absorb a 0.9 weight percent solution of sodium chloride in distilled water at room temperature (test solution) while the material is under a 0.9 psi load. The apparatus for testing AUL consists of:

An AUL assembly including a cylinder, a 4.4 g piston, and a standard 317 gm weight. The components of this assembly are described in additional detail below.

A flat-bottomed square plastic tray that is sufficiently broad to allow the glass frits to lay on the bottom without contact with the tray walls. A plastic tray that is 9" by 9"(22.9 cm×22.9 cm), with a depth of 0.5 to 1" (1.3 cm to 2.5 cm) is commonly used for this test method.

A 9 cm diameter sintered glass frit with a 'C' porosity (25-50 microns). This frit is prepared in advance through equilibration in saline (0.9% sodium chloride in distilled water, by weight). In addition to being washed with at least two portions of fresh saline, the frit must be immersed in saline for at least 12 hours prior to AUL measurements.

Whatman Grade 1, 9 cm diameter filter paper circles.

A supply of saline (0.9% sodium chloride in distilled water, by weight).

Referring to FIG. 5, the cylinder 412 of the AUL assembly 400 used to contain the particulate superabsorbent polymer composition 410 is made from one-inch (2.54 cm) inside diameter thermoplastic tubing machined-out slightly to be sure of concentricity. After machining, a 400 mesh stainless steel wire cloth 414 is attached to the bottom of the cylinder 412 by heating the steel wire cloth 414 in a flame until red hot, after which the cylinder 412 is held onto the steel wire cloth until cooled. A soldering iron can be utilized to touch up the seal if unsuccessful or if it breaks. Care must be taken to maintain a flat smooth bottom and not distort the inside of the cylinder 412.

The 4.4 g piston (416) is made from one-inch diameter solid material (e.g., PLEXIGLAS®) and is machined to closely fit without binding in the cylinder 412.

A standard 317 gm weight 418 is used to provide a 62,053 dyne/cm$^2$ (about 0.9 psi) restraining load. The weight is a cylindrical, 1 inch (2.5 cm) diameter, stainless steel weight that is machined to closely fit without binding in the cylinder.

Unless specified otherwise, a sample 410 corresponding to a layer of at least about 300 gsm. (0.16 g) of superabsorbent polymer composition particles is utilized for testing the AUL. The sample 410 is taken from superabsorbent polymer composition particles that are pre-screened through U.S. standard #30 mesh and retained on U.S. std. #50 mesh. The superabsorbent polymer composition particles can be pre-screened with, for example, a RO-TAP® Mechanical Sieve Shaker Model B available from W. S. Tyler, Inc., Mentor Ohio. Sieving is conducted for about 10 minutes.

The inside of the cylinder 412 is wiped with an antistatic cloth prior to placing the superabsorbent polymer composition particles 410 into the cylinder 412.

The desired amount of the sample of sieved particulate superabsorbent polymer composition 410 (about 0.16 g) is weighed out on a weigh paper and evenly distributed on the wire cloth 414 at the bottom of the cylinder 412. The weight of the particulate superabsorbent polymer composition in the bottom of the cylinder is recorded as 'SA,' for use in the AUL calculation described below. Care is taken to be sure no particulate superabsorbent polymer composition cling to the wall of the cylinder. After carefully placing the 4.4 g piston 412 and 317 g weight 418 on the superabsorbent is polymer composition particles 410 in the cylinder 412, the AUL assembly 400 including the cylinder, piston, weight, and particulate superabsorbent polymer composition particles is weighed, and the weight is recorded as weight 'A'.

A sintered glass frit 424 (described above) is placed in the plastic tray 420, with saline 422 added to a level equal to that of the upper surface of the glass frit 424. A single circle of filter paper 426 is placed gently on the glass frit 424, and the AUL assembly 400 with the particulate superabsorbent polymer composition 410 is then placed on top of the filter paper 426. The AUL assembly 400 is then allowed to remain on top of the filter paper 426 for a test period of one hour, with attention paid to keeping the saline level in the tray constant. At the end of the one hour test period, the AUL apparatus is then weighed, with this value recorded as weight 'B.'

The AUL(0.9 psi) is calculated as follows:

$$AUL(0.9\ psi) = (B - A)/SA$$

wherein

A=Weight of AUL Unit with dry SAP

B=Weight of AUL Unit with SAP after 60 minutes absorption

SA=Actual SAP weight

A minimum of two tests is performed and the results are averaged to determine the AUL value under 0.9 psi load. The particulate superabsorbent polymer composition samples are tested at about 23° C. and about 50% relative humidity.

Free-Swell Gel Bed Permeability Test (FSGBP)

As used herein, the Free-Swell Gel Bed Permeability Test, also referred to as the Gel Bed Permeability Under 0 psi Swell Pressure Test (FSGBP), determines the permeability of a swollen bed of gel particles (e.g., such as the particulate superabsorbent polymer composition, or the particulate superabsorbent polymer prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 2, 3, and 4 and indicated generally as 500. The test apparatus assembly 528 comprises a sample container, generally indicated at 530, and a plunger, generally indicated at 536. The plunger comprises a shaft 538 having a cylinder hole is bored down the longitudinal axis and a head 550 positioned at the bottom of the shaft. The shaft hole 562 has a diameter of about 16 mm. The plunger head is attached to the shaft, such as by adhesion. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm.

The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but can be machined at the top of the shaft to obtain the desired mass of the plunger 536. The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic adhesive, Weld-On #4, from IPS Corporation (having a place of business in Gardena, California, USA) is a suitable adhesive.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic adhesive, Weld-On #4, from IPS Corporation is a suitable adhesive. A gel particle sample, indicated as 568 in FIG. 3, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm$^2$), a wall thickness of about 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of about 0.3 pounds per square inch (psi), or about 20.7 dynes/cm$^2$ (2.07 kPa), over a sample area of about 28.27 cm$^2$.

When the test solution flows through the test apparatus during testing as described below, the sample container 530 generally rests on a weir 600. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568.

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 Newtons. It is important to measure the height of each empty sample container 530, plunger 536, and weight 548 combination and to keep track of which plunger 536 and weight 548 is used when using multiple test apparatus. The same plunger 536 and weight 548 should be used for measurement when the sample 568 is later swollen following saturation. It is also desirable that the base that the sample cup 530 is resting on is level, and the top surface of the weight 548 is parallel to the bottom surface of the sample cup 530.

The sample to be tested is prepared from the particulate superabsorbent polymer composition, which is prescreened through a U.S. standard 30 mesh screen and retained on a U.S. standard 50 mesh screen. As a result, the test sample comprises particles sized in the range of about 300 to about 600 microns. The superabsorbent polymer particles can be pre-screened with, for example, a RO-TAP Mechanical Sieve Shaker Model B available from W. S. Tyler, Inc., Mentor Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then submerged in the 0.9% saline solution for a time period of about 60 minutes to saturate the sample and allow the sample to is swell free of any restraining load. During saturation, the sample cup 530 is set on a mesh located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wisconsin, U.S.A. Saline does not fully cover the superabsorbent polymer composition particles, as would be evidenced by a perfectly flat saline surface in the test cell. Also, saline depth is not allowed to fall so low that the surface within the cell is defined solely by swollen superabsorbent, rather than saline.

At the end of this period, the plunger 536 and weight 548 assembly is placed on the saturated sample 568 in the sample container 530 and then the sample container 530, plunger 536, weight 548, and sample 568 are removed from the solution. After removal and before being measured, the sample container 530, plunger 536, weight 548, and sample 568 are to remain at rest for about 30 seconds on a suitable flat, large grid non-deformable plate of uniform thickness. The thickness of the saturated sample 568 is determined by again measuring the height from the top of the weight 548 to the bottom of the sample container 530, using the same thickness gauge used previously provided that the zero point is unchanged from the initial height measurement. The sample container 530, plunger 536, weight 548, and sample 568 may be placed on a flat, large grid non-deformable plate of uniform thickness that will provide for drainage. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Carr Supply Company, having a place of business in Chicago, Illinois, U.S.A., which can then be cut to the proper dimensions. This flat, large mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software.

The flow rate, Q, through the swollen sample 568 is determined in units of grams/second (g/s) by a linear least-square fit of fluid passing through the sample 568 (in grams) versus time (in seconds).

Permeability in cm² is obtained by the following equation:

$$K = [Q*H*\mu]/[A*\rho*P]$$

where K=Permeability (cm²), Q=flow rate (g/sec), H=height of swollen sample (cm), µ=liquid viscosity (poise) (approximately one centipoise for the test solution used with this Test), A=cross-sectional area for liquid flow (28.27 cm² for the sample container used with this Test), ρ=liquid density (g/cm³) (approximately one g/cm³, for the test solution used with this Test) and P=hydrostatic pressure (dynes/cm²) (normally approximately 7,797 dynes/cm²). The hydrostatic pressure is calculated from P=ρ*g*h, where ρ=liquid density (g/cm³), g=gravitational acceleration, nominally 981 cm/sect, and h=fluid height, e.g., 7.95 cm for the Gel Bed Permeability Test described herein.

A minimum of two samples is tested and the results are averaged to determine the gel bed permeability of the sample of particulate superabsorbent polymer composition.

The FSGBP can be measured as described herein prior to subjecting a particulate superabsorbent polymer composition to a Processing Test as described herein. Such a FSGBP value can be referred to as the "original" FSGBP of the particulate superabsorbent polymer composition. The FSGBP may also be measured subsequent to subjecting the particulate superabsorbent polymer composition to the Processing Test. Such a FSGBP value can be referred to as the "post processing" FSGBP. Comparing the original FSGBP of a particulate superabsorbent polymer composition with the post processing FSGBP of the particulate superabsorbent polymer composition can be used as a measure of the stability of the composition. It should be noted that all "original" and "post processing" FSGBP values reported herein were measured using a sample of pre-screened 300 to 600 µm particles.

The Vortex Test

The Vortex Test measures the amount of time in seconds required for 2 grams of a SAP to close a vortex created by stirring 50 milliliters of saline solution at 600 revolutions per minute on a magnetic stir plate. The time it takes for the vortex to close is an indication of the free swell absorbing rate of the SAP.

Equipment and Materials

1. Schott Duran 100 ml Beaker and 50 ml graduated cylinder.
2. Programmable magnetic stir plate, capable of providing 600 revolutions per minute (such as that commercially available from PMC Industries, under the trade designation Dataplate® Model #721).
3. Magnetic stir bar without rings, 7.9 millimeter-s.times.32 millimeters, Teflon® covered (such as that commercially available from Baxter Diagnostics, under the trade designation S/PRIM. brand single pack round stirring bars with removable pivot ring).
4. Stopwatch
5. Balance, accurate to +/−0.01 g
6. Saline solution, 0.87 w/w % Blood Bank Saline available from Baxter Diagnostics (considered, for the purposes of this application to be the equivalent of 0.9 wt. % saline
7. Weighing paper
8. Room with standard condition atmosphere: Temp=23° C.+1-1° C. and Relative Humidity=50%+1-2%.

Test Procedure

1. Measure 50 ml+/−0.01 ml of saline solution into the 100 ml beaker.
2. Place the magnetic stir bar into the beaker.
3. Program the magnetic stir plate to 600 revolutions per minute.
4. Place the beaker on the center of the magnetic stir plate such that the magnetic stir bar is activated. The bottom of the vortex should be near the top of the stir bar.
5. Weigh out 2g+/−0.01 g of the SAP to be tested on weighing paper.
NOTE: The SAP is tested as received (i.e. as it would go into an absorbent composite such as those described herein). No screening to a specific particle size is done, though the particle size is known to have an effect on this test.
6. While the saline solution is being stirred, quickly pour the SAP to be tested into the saline solution and start the stopwatch. The SAP to be tested should be added to the saline solution between the is center of the vortex and the side of the beaker.
7. Stop the stopwatch when the surface of the saline solution becomes flat and record the time.
8. The time, recorded in seconds, is reported as the Vortex Time.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

We claim:

1. An absorbent product comprising:
   a liquid permeable bodyside liner;
   a liquid impermeable barrier layer; and
   an absorbent body positioned between the liquid permeable bodyside and the liquid impermeable barrier layer, the absorbent body comprising:
   a top nonwoven layer comprising synthetic fibers forming a liquid permeable web material;
   a bottom nonwoven layer comprising synthetic fibers forming a web material;
   a fibrous nonwoven through-air-bonded-carded web (TABCW) reinforcement layer disposed between the top layer and the bottom layer where the top layer and the bottom layer are bonded directly together and enclose the reinforcement layer, the reinforcement layer having absorbent material embedded within fibers of the reinforcement layer;
   a first absorbent layer disposed between the reinforcement layer and the bottom layer, the first absorbent layer comprising absorbent material which comprises substantially only superabsorbent material;
   a second absorbent layer disposed between the top layer and the reinforcement layer, the second absorbent layer comprising a mixed layer of superabsorbent material and fibrous absorbent material; and
   adhesive disposed between the top layer and the second absorbent layer, between the second absorbent layer and the reinforcement layer, and between the first absorbent layer and the bottom layer.

2. The absorbent body of claim 1, wherein the absorbent material of the second absorbent layer comprises substantially only fibrous absorbent material.

3. The absorbent body of claim 1, wherein the absorbent material of the second absorbent layer comprises substantially only superabsorbent material.

4. The absorbent body of claim 1, wherein the absorbent material disposed within the second absorbent layer comprises between about 50% and about 80%, by weight, of superabsorbent material.

5. The absorbent body of claim 4, wherein the absorbent material disposed within the second absorbent layer comprises a mixture of superabsorbent material and fibrous absorbent material, and wherein the mixture comprises a substantially uniform distribution of the superabsorbent material and the fibrous absorbent material.

6. The absorbent body of claim 1, wherein the superabsorbent material embedded within the reinforcement layer comprises between about 50% and about 80%, by weight, of the superabsorbent material embedded within the reinforcement layer and the superabsorbent material disposed within the first absorbent layer.

7. The absorbent body of claim 1, wherein the superabsorbent material embedded within the reinforcement layer comprises between about 50% and about 65%, by weight, of the superabsorbent material embedded within the reinforcement layer and the superabsorbent material disposed within the first absorbent layer.

8. The absorbent body of claim 1, wherein a total weight of absorbent material disposed within the second absorbent layer is between about 5 g and about 20 g.

9. The absorbent body of claim 1, wherein a total weight of absorbent material embedded within the reinforcement layer and disposed within the first absorbent layer is between about 5 g and about 15 g.

10. The absorbent body of claim 1, wherein the total amount of absorbent material embedded within the reinforcement layer and disposed within the first absorbent layer is between about 50% and about 60%, by weight, of the total amount of absorbent material disposed within the first absorbent layer, the second absorbent layer, and embedded within the reinforcement layer.

11. The absorbent body of claim 1, further comprising an airlaid paper layer disposed between the second absorbent layer and the liquid permeable top-layer.

12. The absorbent body of claim 1, further comprising an airlaid paper layer disposed between the first absorbent layer and the bottom layer.

13. The absorbent body of claim 1, further comprising a third absorbent layer, wherein: the third absorbent layer is disposed between the second absorbent layer and the top layer, and the third absorbent layer comprises absorbent material comprising substantially only superabsorbent material.

14. The absorbent body of claim 1, wherein the first absorbent layer comprises at least one channel region and a plurality of non-channel regions, and wherein an absorbent material content of the non-channel regions is greater than an absorbent material content of the at least one channel region.

* * * * *